(12) United States Patent
Han et al.

(10) Patent No.: US 12,105,075 B2
(45) Date of Patent: Oct. 1, 2024

(54) TOTAL NITROGEN INTELLIGENT DETECTION METHOD BASED ON MULTI-OBJECTIVE OPTIMIZED FUZZY NEURAL NETWORK

(71) Applicant: BEIJING UNIVERSITY OF TECHNOLOGY, Beijing (CN)

(72) Inventors: Honggui Han, Beijing (CN); Chenxuan Sun, Beijing (CN); Junfei Qiao, Beijing (CN)

(73) Assignee: BEIJING UNIVERSITY OF TECHNOLOGY, Beijing (CN)

( * ) Notice: Subject to any disclaimer, the term of this patent is extended or adjusted under 35 U.S.C. 154(b) by 369 days.

(21) Appl. No.: 17/472,433

(22) Filed: Sep. 10, 2021

(65) Prior Publication Data
US 2022/0082545 A1    Mar. 17, 2022

(30) Foreign Application Priority Data
Sep. 15, 2020    (CN) .......................... 202010964415.6

(51) Int. Cl.
*G06N 3/043*        (2023.01)
*C02F 1/00*         (2023.01)
(Continued)

(52) U.S. Cl.
CPC ......... *G01N 33/1806* (2013.01); *G06N 3/043* (2023.01); *G06N 3/08* (2013.01); *C02F 1/008* (2013.01); *C02F 2209/16* (2013.01)

(58) Field of Classification Search
CPC .... G01N 33/1806; G01N 33/18; G06N 3/043; G06N 3/08; G06N 3/006; C02F 1/008; (Continued)

(56) References Cited

U.S. PATENT DOCUMENTS

| | | | | |
|---|---|---|---|---|
| 10,570,024 | B2 * | 2/2020 | Han | G06N 3/088 |
| 10,919,791 | B2 * | 2/2021 | Han | G06F 30/27 |

(Continued)

FOREIGN PATENT DOCUMENTS

| | | | | |
|---|---|---|---|---|
| CN | 109669352 A | * | 4/2019 | G05B 13/04 |
| CN | 111291937 A | * | 6/2020 | |

*Primary Examiner* — Douglas Kay
(74) *Attorney, Agent, or Firm* — J.C. PATENTS

(57) ABSTRACT

A total nitrogen intelligent detection system based on multi-objective optimized fuzzy neural network belongs to both the field of environment engineer and control engineer. The total nitrogen in wastewater treatment process is an important index to measure the quality of effluent. However, it is extremely difficult to detect the total nitrogen concentration due to the long detection time and the low prediction accuracy in the wastewater treatment process. To solve the problem, multi-objective optimized fuzzy neural network with global optimization capability may be established to optimize the structure and parameters to solve the problem of the poor generalization ability of fuzzy neural network. The experimental results show that total nitrogen intelligent detection system can automatically collect the variables information of wastewater treatment process and predict total nitrogen concentration. Meanwhile, in this system, the detection method can improve the prediction accuracy, as well as ensure the total nitrogen concentration be obtained in real-time and low-cost.

2 Claims, 5 Drawing Sheets

(51) Int. Cl.
*G01N 33/18* (2006.01)
*G06N 3/08* (2023.01)

(58) Field of Classification Search
CPC .............. C02F 2209/16; C02F 2209/04; C02F 2209/06; C02F 2209/08; C02F 2209/14; C02F 2209/15
See application file for complete search history.

(56) References Cited

U.S. PATENT DOCUMENTS

2018/0029900 A1\* 2/2018 Han ........................ C02F 1/008
2020/0024168 A1\* 1/2020 Han ........................ G06F 30/27

\* cited by examiner

TOTAL NITROGEN INTELLIGENT DETECTION METHOD BASED ON MULTI-OBJECTIVE OPTIMIZED FUZZY NEURAL NETWORK

CROSS-REFERENCE TO RELATED APPLICATIONS

This application claims priority to Chinese Patent Application No. 202010964415.6, filed on Sep. 15, 2020, which is hereby incorporated by reference in its entirety and made a part of this specification.

TECHNOLOGY AREA

In this disclosure, a computing method is established for realizing the total nitrogen intelligent detection by a fuzzy neural network with multi-objective particle swarm optimization algorithm. This method based on the multi-objective optimized fuzzy neural network can improve the generalization ability of the model by fully learning the multiple objective functions to enhance the prediction accuracy of total nitrogen. The method belongs to both the field of control engineer and environmental engineer, which is an important branch for the field of advanced manufacturing technology.

TECHNOLOGY BACKGROUND

The serious water pollution has highlighted the problem of water shortage in the world, and it has become a problem that cannot be ignored to ensure the health and production of people. With the acceleration of the urbanization process, the demand for freshwater resources is increasing, resulting in an increasing amount of wastewater. However, wastewater is recognized as a stable freshwater resource. Its recycling can not only reduce the demand for natural water but also reduce the pollution of the environment, which is an indispensable measure to ensure the water cycle. World Water Development Report pointed out that the innovative technology was used to acquire knowledge by collecting and processing the water information and data, which will help to further improve water resources management. Therefore, the research results of wastewater treatment technology have broad application prospects.

With the improvement of wastewater treatment technology, the pollution of organic matter in the wastewater has been curbed, but the excessive discharge of nutrients such as nitrogen and phosphorus has caused serious water pollution. The increase of nitrogen content is one of the main factors that cause the deterioration of water quality and eutrophication. At the same time, the total nitrogen is also used as an evaluation indicator in many national standards. At present, wastewater treatment plants mainly detect total nitrogen concentration through chemical experiments. Although this method can guarantee accurate detection accuracy, it has high requirements on the operating environment and detection time, which requires a long detection time. However, the accurate and rapid detection of total nitrogen play a great significance in the prevention of water pollution and regeneration.

In order to achieve real-time and high-precision detection of total nitrogen, artificial neural networks have become a mainstream technology. The neural network with nonlinear approximation ability and learning ability can establish a nonlinear method of the wastewater treatment process, which provides a new method for wastewater detection. Hence, the novel method presented to realize the real-time and high-precision measurement has an important topic.

To solve the problem, the invention designed an intelligent detection method for total nitrogen based on multi-objective optimized fuzzy neural network. In this method, data can be automatically acquired and the total nitrogen concentration can be detected in real-time to improve the level of intelligence. The model adopt a multi-objective particle swarm optimization algorithm with global optimization capabilities to optimize the multi-level learning objectives of fuzzy neural network to adjust the parameters and structure, which can improve the generalization performance of the network. This method was able to realize the accurate detection of total nitrogen by improving the generalization ability, which can realize the actual demand of the wastewater treatment plant.

SUMMARY

The invention proposed a total nitrogen intelligent detection method based on fuzzy neural network. This method used the least squares algorithm to extract feature variables to determine the main variables related to the total nitrogen and automatically collect data by transmission devices. Then, based on the multi-level learning objectives of fuzzy neural network, the multi-objective particle swarm algorithm was used to optimize the parameters and structure simultaneously. This method solved the problem of poor generalization ability and had better detection accuracy than traditional fuzzy neural networks.

The total nitrogen intelligent detection method includes the following steps: (1) Selecting input variables and collecting data by transmission devices, (2) Establishing an initial fuzzy neural network, (3) Training the fuzzy neural network based on multi-objective particle swarm optimization algorithm, (4) Total nitrogen concentration prediction.

(1) Selecting Input Variables and Collecting Data by Transmission Devices

Through the analysis of the wastewater treatment process, a least square method is used to extract feature variables; then, dosage, oxidation-reduction potential, orthophosphate, pH, ammonia nitrogen, nitrate-nitrogen and chemical oxygen demand are the feature variables that affect the total nitrogen concentration; each variable was measured by the dosage device, the oxidation-reduction potential sensor, the orthophosphate sensor, pH detector, the ammonia nitrogen sensor, the nitrate-nitrogen sensor and the chemical oxygen demand sensor, and then transmitted to the model of the computer by optical fiber communication network; where the dosage device is at an end of a second aerobic tank, the oxidation-reduction potential sensor in a middle of an anaerobic tank, the orthophosphate sensor at an end of the second aerobic tank, the pH detector in an inlet cell, the ammonia nitrogen sensor in the inlet cell, the nitrate-nitrogen sensor at the end of the first anoxic tank and the chemical oxygen demand sensor is at the end of a primary sedimentation tank; the sensors use probes to achieve variables concentration detection, and dosage device uses a flow meter to achieve detection; the feature variables are obtained by devices and normalized to [0, 1], and the total nitrogen concentration is normalized to [0, 1];

(2) Establishing an Initial Fuzzy Neural Network

A total nitrogen intelligent detection model based on fuzzy neural network contains four layers: an input layer, a membership function layer, a rule layer and an output layer; the fuzzy neural network is 7-P-Q-1, including 7 neurons in the input layer, P neurons in the membership function layer, Q neurons in the rule layer and a neurons in the output layer, P and Q are positive integers between [2, 15], and P=Q; the number of training samples is N, an input of the fuzzy neural network is $x(n)=[x_1(n), x_2(n), \ldots, x_7(n)]$, $x_1(n)$ represents the dosage in nth sample; $x_2(n)$ represents the oxidation-reduction potential in the middle of anaerobic tank in nth sample, $x_3(n)$ represents the orthophosphate at the end of the second aerobic tank in nth sample, $x_4(n)$ represents pH in the inlet cell in nth sample, $x_5(n)$ represents the ammonia nitrogen in the inlet cell in nth sample, $x_6(n)$ represents the nitrate nitrogen at the end of the anoxic tank in nth sample, and $x_7(n)$ represents the chemical oxygen demand of the primary sedimentation tank in nth sample, the output of fuzzy neural network is $y(n)$ and the actual output is $\hat{y}(n)$, $n=1, 2, \ldots, N$; the fuzzy neural network includes:

① input layer: there are 7 neurons in the input layer, an output of the input layer is:

$$u_m(n)=x_m(n), m=1,2,\ldots 7 \quad (1)$$

where $u_m(n)$ is mth output value, $m=1, 2, \ldots, 7$;

② membership function layer: there are P neurons in the membership function layer, an output of the membership function layer is:

$$\varphi_p(n) = \prod_{i=1}^{7} e^{-\frac{(u_m(n)-\mu_{mp}(n))^2}{2\sigma_p^2(n)}} = e^{-\sum_{m=1}^{7}\frac{(u_m(n)-\mu_{mp}(n))^2}{2\sigma_p^2(n)}}, \quad (2)$$

$$p = 1, 2, \ldots, P$$

where $\mu_{mp}(n)$ is a center of pth membership function neuron with mth input, $\sigma_p(n)$ is the standard deviation of pth membership function neuron, $\varphi_p(n)$ is the output value of pth membership function;

③ rule layer: there are Q neurons in the rule layer, and an output value of the rule layer is:

$$\eta_q(n) = \varphi_q(n) \Big/ \sum_{p=1}^{P} \varphi_p(n), \quad q = 1, 2, \ldots, Q \quad (3)$$

where $\eta_q(n)$ is an output of qth neuron;

④ output layer: there is a neuron in the output layer, and an output value of the output layer is:

$$y(n) = \sum_{q=1}^{Q} w_q(n)\eta_q(n), \quad q = 1, 2, \ldots, Q \quad (4)$$

where $y(n)$ is an output value of fuzzy neural network, $w_q(n)$ is connection weight between qth neuron in the rule layer and the output layer neuron.

(3) Training the Fuzzy Neural Network Based on Multi-Objective Particle Swarm Optimization Algorithm ① In the fuzzy neural network, each variable in an initial center vector $\mu_q(1)$ is randomly selected in the interval $[-1, 1]$, an initial width $\sigma_q(1)$ is assigned to 1, $q=1, 2, \ldots, Q$; each variable in an initial connection weight vector $w(1)$ is randomly selected in the interval $[-1, 1]$; and set a current iteration number $t=1$.

② Set maximum number of iterations is $T_{max}$, $T_{max} \in [200, 500]$; the number of particles in a population of the multi-objective particle swarm optimization algorithm is L, $L \in [50, 150]$, and each particle represents a fuzzy neural network; maximum number of neurons in the rule layer is 15, so fixed maximum dimension of the particle is set to 135, and each particle is represented by a 135-dimensional row vector; position and velocity of lth particle can be expressed as:

$$a_l(1)=[\mu_{l,1}(1),\sigma_{l,1}(1),w_{l,1}(1),\mu_{l,2}(1),\sigma_{l,2}(1),w_{l,2}(1),\ldots,\mu_{l,Q_l(1)}(1),\sigma_{l,Q_l(1)}(1),w_{l,Q_l(1)}(1)] \quad (5)$$

$$v_l(1)=[v_{l,1}(1),v_{l,2}(1),\ldots,v_{l,9Q_l(1)}(1)] \quad (6)$$

where $l=1, 2, \ldots, L$, $a_l(1)$ represents a position vector of initial lth particle, $\mu_{l,k}(1)$, $\sigma_{l,k}(1)$, $w_{l,k}(1)$ represent a center vector, width and connection weight of kth neuron in the fuzzy neural network rule layer corresponding to the initial lth particle, respectively, $k=1, 2, \ldots, Q_l(1)$, $Q_l(1)$ is the number of rule layer neurons corresponding to the initial lth particle, $vi(1)$ represents an initial velocity vector of the lth particle; an initial position vector $a_l(1)$ is determined by parameters and structure of initial fuzzy neural network; each variable of the initial velocity vector $v_l(1)$ can take any value in $[-0.5, 0.5]$; initial effective dimension of the lth particle is $9Q_l(1)$; when the effective particle dimension is less than 135, values of remaining dimensions are filled with 0 to ensure consistency of the particle dimensions in the population.

③ The objective functions of multi-objective particle swarm optimization algorithm include accuracy and complexity of the fuzzy neural network; the accuracy of the fuzzy neural network is represented by a root mean square error, so the designed objective function is:

$$f_1(a_l(t)) = \sqrt{\sum_{n=1}^{N}(y_l(n)-\hat{y}(n))^2 \Big/ N} \quad (7)$$

where $y_l(n)$ is a predicted output value of the fuzzy neural network corresponding to the lth particle $a_l(t)$, $\hat{y}(n)$ is an actual output value of the training sample, and $f_1(a_l(t))$ is a first objective function value corresponding to the particle $a_l(t)$ at the tth iteration. In addition, the objective function based on structure complexity is designed as:

$$f_2(a_l(t)) = (15Q_l(t)\log N + 2\log Q_l(t))\sum_{n=1}^{N}(y_l(n)-\hat{y}(n))^2 \Big/ N\sum_{n=1}^{N}(\hat{y}(n)-\bar{y})^2 \quad (8)$$

$$\bar{y} = \sum_{n=1}^{N}\hat{y}(n)/N \quad (9)$$

where $Q_l(t)$ is the number of neurons in the layer corresponding to the lth particle at the tth iteration, $\bar{y}$ is average output value of the N training samples, $f_2(a_l(t))$ is a second objective function value corresponding to the particle $a_l(t)$ at the tth iteration.

④ According to the function values $f_1(a_l(t))$ and $f_2(a_l(t))$ of multi-objective particle swarm optimization algorithm, crowded distances of particles in an objective space and a decision space are as follows:

$$S_O(a_l(t)) = \sqrt{\sum_{j=1}^{L}((f_1(a_l(t))-f_1(a_j(t)))^2+(f_2(a_l(t))-f_2(a_j(t)))^2)} \quad (10)$$

-continued $$S_D(a_l(t)) = \sqrt{\sum_{j=1}^{L}(a_l(t)-a_j(t))^2} \qquad (11)$$

where $S_O(a_l(t))$ is the crowded distance of the particle $a_l(t)$ in the objective space at the tth iteration, and $S_D(a_l(t))$ is the crowded distance of the particle $a_l(t)$ in the decision space at the tth iteration; based on the diversity and convergence of particles, a global optimal particle is selected:

$$G_R(a_l(t)) = \frac{\sqrt{(f_1(a_l(t)))^2 + (f_2(a_l(t)))^2}}{S'_O(a_l(t)) + S'_D(a_l(t))} \qquad (12)$$

where $G_R(a_l(t))$ is a comprehensive index value of particle $a_l(t)$ in the population at the tth iteration, as well as $S'_O(a_l(t))$ and $S'_D(a_l(t))$ are respectively $S_O(a_l(t))$ and $S_D(a_l(t))$ normalized crowding distance; the particle $a_l(t)$ with smallest $G_R(a_l(t))$ value in the population is the global optimal particle at the tth iteration.

⑤ Update dth dimensional velocity and position of the particle is:

$$v_{l,d}(t+1) = \omega v_{l,d}(t) + c_1 r_1(p_{l,d}(t) - a_{l,d}(t)) + c_2 r_2(g_d(t) - a_{l,d}(t)) \qquad (13)$$

$$a_{l,d}(t+1) = a_{l,d}(t) + v_{l,d}(t+1) \qquad (14)$$

where $v_{l,d}(t)$ represents the dth dimensional velocity of the lth particle at the tth iteration, $a_{l,d}(t)$ represents the dth dimensional position of the lth particle at the tth iteration, $v_{l,d}(t+1)$ and $a_{l,d}(t+1)$ represent the dth dimensional velocity and position of the lth particle at the t+1 iteration, d=1, 2, ..., 135; an extra particle dimension is set to 0; $\omega$ is a weight of inertia, $\omega$ can be arbitrarily selected in [0, 1], $c_1$ is individual learning factors, and $c_1$ is arbitrarily selected in [1.5, 2]; $c_2$ is global learning factors, and $c_2$ is arbitrarily selected in [1.5, 2]; $r_1$ and $r_2$ represent random values uniformly distributed between [0, 1], $p_l(t)=[p_{l,1}(t), p_{l,2}(t), \ldots, p_{l,135}(t)]$, $p_l(t)$ is the lth individual optimal particle at the tth iteration, $g(t)=[g_1(t), g_2(t), \ldots g_{135}(t)]$, $g(t)$ is the global optimal particle at the tth iteration.

⑥ If mod (t, 5)≠0 and t<$T_{max}$, the number of iterations t will increase by 1, and go to step ③; if mod (t, 5)=0 and t<$T_{max}$, go to step ⑦; if t=$T_{max}$, stop training process; mod ( ) is the remainder operation.

⑦ Update rules of the fuzzy neural network structure are as follows:

$$Q_l(t+1) = Q_l(t) + h \qquad (15)$$

$$Q_{ave}(t) = \sum_{i=0}^{4} Q_g(t-i)/5 \qquad (16)$$

when $Q_{ave}(t)<Q_l(t)$, h=−1; when $Q_{ave}(t)=Q_l(t)$, h=0; when $Q_{ave}(t)>Q_l(t)$, h=1; $Q_g(t)$ is the number of neurons in the rule layer corresponding to the global optimal particle $g(t)$ at the tth iteration, i is the difference with the current iteration number, i=0, 1, ..., 4, $Q_l(t+1)$ represents the number of neurons in the rule layer corresponding to the t+1 iteration of the lth particle.

⑧ If t<$T_{max}$, the number of iterations t increase by 1, and go to step ③; if t=$T_{max}$, stop the training process.

(4) Total Nitrogen Concentration Prediction

The dosage, the oxidation-reduction potential in the middle of the anaerobic tank, the orthophosphate at the end of the second aerobic tank, pH in the inlet cell, the ammonia nitrogen in the inlet cell, the nitrate-nitrogen at the end of the anoxic tank and the chemical oxygen demand of the primary sedimentation tank are used as the input of the detection model; then the output value of the detection model is got and anti-normalized it to obtain the detection value of the total nitrogen concentration.

In an embodiment, the transmission device is used to transmit the received real-time data information to the fuzzy neural network as input. The data sets in the sensors are transmitted to the computer through the optical fiber communication network, and the computer is sent to the detection model by the Ethernet to realize the detection of the total nitrogen concentration.

The Novelties of this Patent Contain:

(1) Aiming at the long detection time of total nitrogen in the wastewater treatment process, the present invention proposed a total nitrogen intelligent detection method, which solved the problem through automatic collection technology and intelligent detection methods based on fuzzy neural network.

(2) Aiming at the problem that a single learning objective is difficult to improve the generalization ability of fuzzy neural network, the invention developed multi-level generalization indicators, which used the multi-level generalization indicators as the objective functions for constructing the parameters and structure to make up for the shortcomings of a single objective.

(3) According to the multi-level learning functions, the method used an improved multi-objective particle swarm optimization algorithm to optimize the parameters and structure, so that the constructed model had suitable training accuracy and network structure. The method designed the model from the perspective of improving the generalization ability to solve the problems, which achieved the low-cost and high-precision detection requirements of the wastewater treatment plant.

BRIEF DESCRIPTION OF DRAWINGS

The detailed description is described with reference to the figures.

DETAILED DESCRIPTION OF THE INVENTION

Figure 1:
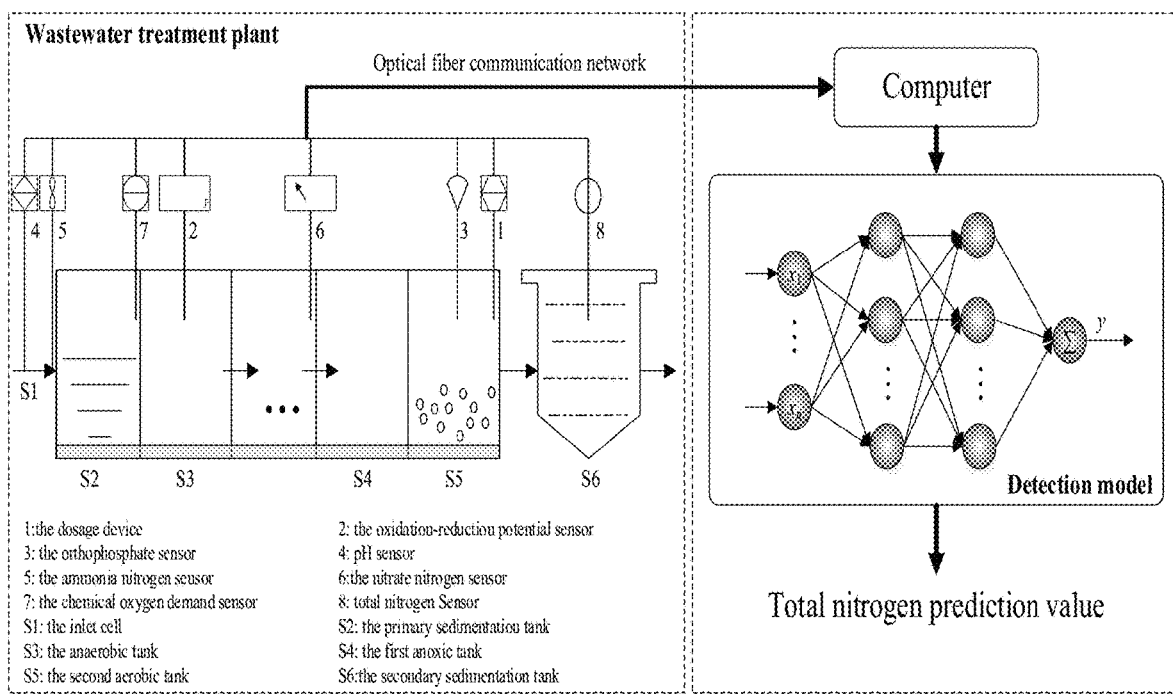
FIG. 1 shows the overall flow chart of the presented method.

The experimental data comes from the wastewater treatment plant. The data sets include the dosage, the oxidation-reduction potential in the middle of the anaerobic tank, the orthophosphate at the end of the second aerobic tank, pH in the inlet cell, the ammonia nitrogen in the inlet cell, the nitrate-nitrogen at the end of the anoxic tank and the chemical oxygen demand of the primary sedimentation tank. After eliminating the abnormal experimental samples, there are 500 sets of available data, where 350 sets are used as training samples and the remaining 150 sets are used as test samples.

A total nitrogen intelligent detection method based on multi-objective optimized fuzzy neural network comprises the following steps:

(1) Selecting Input Variables and Collecting Data by Transmission Devices

Through the analysis of the wastewater treatment process, a least square method is used to extract feature variables; then, dosage, oxidation-reduction potential, orthophosphate, pH, ammonia nitrogen, nitrate-nitrogen and chemical oxygen demand are the feature variables that affect the total nitrogen concentration; each variable was measured by a dosage device 1, an oxidation-reduction potential sensor 2, an orthophosphate sensor 3, a pH detector 4, an ammonia nitrogen sensor 5, a nitrate-nitrogen sensor 6 and a chemical oxygen demand sensor 7, and then transmitted to the model of the computer by optical fiber communication network; where the dosage device is at an end of a second aerobic tank S5, the oxidation-reduction potential sensor 2 in a middle of the anaerobic tank S3, the orthophosphate sensor 3 at an end of the second aerobic tank S5, the pH detector 4 in the inlet cell S1, the ammonia nitrogen sensor 5 in the inlet cell S1, the nitrate-nitrogen sensor 6 at the end of the first anoxic tank S4 and the chemical oxygen demand sensor 7 is at the end of the primary sedimentation tank S2; a total nitrogen sensor 8 is located in a secondary sedimentation tank S6 for measuring the actual total nitrogen concentration, the secondary sedimentation tank S6 is located downstream of the second aerobic tank S5; the sensors use probes to achieve variables concentration detection, and the dosage device uses a flow meter to achieve detection; the feature variables are obtained by devices and normalized to [0, 1], and the total nitrogen concentration is normalized to [0, 1];

(2) Establishing an Initial Fuzzy Neural Network

A total nitrogen intelligent detection model based on fuzzy neural network contains four layers: an input layer, a membership function layer, a rule layer and an output layer; the fuzzy neural network is 7-P-Q-1, including 7 neurons in the input layer, P neurons in the membership function layer, Q neurons in the rule layer and a neurons in the output layer, P and Q are positive integers between [2, 15], and P=Q; the number of training samples is N, an input of the fuzzy neural network is $x(n)=[x_1(n), x_2(n), \ldots, (n)]$, $x_1(n)$ represents the dosage in nth sample; $x_2(n)$ represents the oxidation-reduction potential in the middle of anaerobic tank in nth sample, $x_3(n)$ represents the orthophosphate at the end of the second aerobic tank in nth sample, $x_4(n)$ represents pH in the inlet cell in nth sample, $x_5(n)$ represents the ammonia nitrogen in the inlet cell in nth sample, $x_6(n)$ represents the nitrate nitrogen at the end of the anoxic tank in nth sample, and $x_7(n)$ represents the chemical oxygen demand of the primary sedimentation tank in nth sample, the output of fuzzy neural network is y(n) and the actual output is $\hat{y}(n)$, n=1, 2, ..., N; the fuzzy neural network includes:

① input layer: there are 7 neurons in the input layer, an output of the input layer is:

$$u_m(n)=x_m(n), m=1,2,\ldots,7 \quad (1)$$

where $u_m m(n)$ is mth output value, m=1, 2, ..., 7;

② membership function layer: there are P neurons in the membership function layer, an output of the membership function layer is:

$$\varphi_p(n) = \prod_{i=1}^{7} e^{-\frac{(u_m(n)-\mu_{mp}(n))^2}{2\sigma_p^2(n)}} = e^{-\sum_{m=1}^{7} \frac{(u_m(n)-\mu_{mp}(n))^2}{2\sigma_p^2(n)}}, \quad (2)$$

$$p = 1, 2, \ldots, P$$

where $\mu_{mp}(n)$ is a center of pth membership function neuron with mth input, $\sigma_p(n)$ is the standard deviation of pth membership function neuron, $\varphi_p(n)$ is the output value of pth membership function;

③ rule layer: there are Q neurons in the rule layer, and an output value of the rule layer is:

$$\eta_q(n) = \varphi_q(n) \bigg/ \sum_{p=1}^{P} \varphi_p(n), q = 1, 2, \ldots, Q \quad (3)$$

where $\eta_q(n)$ is an output of qth neuron;

④ output layer: there is a neuron in the output layer, and an output value of the output layer is:

$$y(n) = \sum_{q=1}^{Q} w_q(n)\eta_q(n), q = 1, 2, \ldots, Q \quad (4)$$

where y(n) is an output value of fuzzy neural network, $w_q(n)$ is connection weight between qth neuron in the rule layer and the output layer neuron.

(3) Training the fuzzy neural network based on multi-objective particle swarm optimization algorithm ① In the fuzzy neural network, each variable in an initial center vector $\mu_q(1)$ is randomly selected in the interval [−1, 1], an initial width $\sigma_q(1)$ is assigned to 1, q=1, 2, ..., Q; each variable in an initial connection weight vector w(1) is randomly selected in the interval [−1, 1]; and set a current iteration number t=1.

② Set the maximum number of iterations is $T_{max}$, $T_{max} \in [200, 500]$; the number of particles in a population of the multi-objective particle swarm optimization algorithm is L, L∈ [50, 150], and each particle represents a fuzzy neural network; maximum number of neurons in the rule layer is 15, so fixed maximum dimension of the particle is set to 135, and each particle is represented by a 135-dimensional row vector; position and velocity of lth particle can be expressed as:

$$a_l(1)=[\mu_{l,1}(1),\sigma_{l,1}(1),w_{l,1}(1),\mu_{l,2}(1),\sigma_{l,2}(1),w_{l,2}(1),\ldots,\mu_{l,Q_l(1)}(1),\sigma_{l,Q_l(1)}(1),w_{l,Q_l(1)}(1)] \quad (5)$$

$$v_l(1)=[v_{l,1}(1),v_{l,2}(1),\ldots,v_{l,9Q_l(1)}(1)] \quad (6)$$

where l=1, 2, ..., L, $a_l(1)$ represents a position vector of initial lth particle, $\mu_{l,k}(1)$, $\sigma_{l,k}(1)$, $w_{l,k}(1)$ represent a center vector, width and connection weight of kth neuron in the fuzzy neural network rule layer corresponding to the initial lth particle, respectively, k=1, 2, ..., $Q_l(1)$, $Q_l(1)$ is the number of rule layer neurons corresponding to the initial lth particle, $v_l(1)$ represents an initial velocity vector of the lth particle; an initial position vector $a_l(1)$ is determined by parameters and structure of initial fuzzy neural network;

each variable of the initial velocity vector $v_l(1)$ can take any value in $[-0.5, 0.5]$; initial effective dimension of the lth particle is $9Q_l(1)$; when the effective particle dimension is less than 135, values of remaining dimensions are filled with 0 to ensure consistency of the particle dimensions in the population.

③ The objective functions of multi-objective particle swarm optimization algorithm include: accuracy and complexity of the fuzzy neural network; the accuracy of the fuzzy neural network is represented by a root mean square error, so the designed objective function is:

$$f_1(a_l(t)) = \sqrt{\sum_{n=1}^{N}(y_l(n) - \hat{y}(n))^2 / N} \tag{7}$$

where $y_l(n)$ is a predicted output value of the fuzzy neural network corresponding to the lth particle $a_l(t)$, $\hat{y}(n)$ is an actual output value of the training sample, and $f_1(a_l(t))$ is a first objective function value corresponding to the particle $a_l(t)$ at the tth iteration. In addition, the objective function based on structure complexity is designed as:

$$f_2(a_l(t)) = (15Q_l(t)\log N + 2\log Q_l(t))\sum_{n=1}^{N}(y_l(n) - \hat{y}(n))^2 / N\sum_{n=1}^{N}(\hat{y}(n) - \bar{y})^2 \tag{8}$$

$$\bar{y} = \sum_{n=1}^{N}\hat{y}(n)/N \tag{9}$$

where $Q_l(t)$ is the number of neurons in the layer corresponding to the lth particle at the tth iteration, $\hat{y}$ is average output value of the N training samples, $f_2(a_l(t))$ is a second objective function value corresponding to the particle $a_l(t)$ at the tth iteration.

④ According to the function values $f_1(a_l(t))$ and $f_2(a_l(t))$ of multi-objective particle swarm optimization algorithm, crowded distances of particles in an objective space and a decision space are as follows:

$$S_O(a_l(t)) = \sqrt{\sum_{j=1}^{L}((f_1(a_l(t)) - f_1(a_j(t)))^2 + (f_2(a_l(t)) - f_2(a_j(t)))^2)} \tag{10}$$

$$S_D(a_l(t)) = \sqrt{\sum_{j=1}^{L}(a_l(t) - a_j(t))^2} \tag{11}$$

where $S_O(a_l(t))$ is the crowded distance of the particle $a_l(t)$ in the objective space at the tth iteration, and $S_D(a_l(t))$ is the crowded distance of the particle $a_l(t)$ in the decision space at the tth iteration; based on the diversity and convergence of particles, a global optimal particle is selected:

$$G_R(a_l(t)) = \frac{\sqrt{(f_1(a_l(t)))^2 + (f_2(a_l(t)))^2}}{S'_O(a_l(t)) + S'_D(a_l(t))} \tag{12}$$

where $G_R(a_l(t))$ is a comprehensive index value of particle $a_l(t)$ in the population at the tth iteration, as well as $S'_O(a_l(t))$ and $S'_D(a_l(t))$ are respectively $S_O(a_l(t))$ and $S_D(a_l(t))$ normalized crowding distance; the particle $a_l(t)$ with smallest $G_R(a_l(t))$ value in the population is the global optimal particle at the tth iteration.

⑤ Update dth dimensional velocity and position of the particle is:

$$v_{l,d}(t+1) = \omega v_{l,d}(t) + c_1 r_1 (p_{l,d}(t) - \alpha_{l,d}(t)) + c_2 r_2 (g_d(t) - \alpha_{l,d}(t)) \tag{13}$$

$$\alpha_{l,d}(t+1) = \alpha_{l,d}(t) + v_{l,d}(t+1) \tag{14}$$

where $v_{l,d}(t)$ represents the dth dimensional velocity of the lth particle at the tth iteration, $\alpha_{l,d}(t)$ represents the dth dimensional position of the lth particle at the tth iteration, $v_{l,d}(t+1)$ and $\alpha_{l,d}(t+1)$ represent the dth dimensional velocity and position of the lth particle at the t+1 iteration, d=1, 2, ..., 135; an extra particle dimension is set to 0; $\omega$ is a weight of inertia, co can be arbitrarily selected in [0, 1], $c_1$ is individual learning factors, and $c_1$ is arbitrarily selected in [1.5, 2]; $c_2$ is global learning factors, and $c_2$ is arbitrarily selected in [1.5, 2]; $r_1$ and $r_2$ represent random values uniformly distributed between [0, 1], $p_l(t) = [p_{l,1}(t), p_{l,2}(t), ..., p_{l,135}(t)]$, $p_l(t)$ is the lth individual optimal particle at the tth iteration, $g(t) = [g_1(t), g_2(t), ..., g_{135}(t)]$, $g(t)$ is the global optimal particle at the tth iteration.

⑥ If mod $(t, 5) \neq 0$ and $t < T_{max}$, the number of iterations t will increase by 1, and go to step ③; if mod $(t, 5) = 0$ and $t < T_{max}$, go to step ⑦; if $t = T_{max}$, stop training process; mod ( ) is the remainder operation.

⑦ Update rules of the fuzzy neural network structure are as follows:

$$Q_l(t+1) = Q_l(t) + h \tag{15}$$

$$Q_{ave}(t) = \sum_{i=0}^{4} Q_g(t-i)/5 \tag{16}$$

when $Q_{ave}(t) < Q_l(t)$, h=-1; when $Q_{ave}(t) = Q_l(t)$, h=0; when $Q_{ave}(t) > Q_l(t)$, h=1; $Q_g(t)$ is the number of neurons in the rule layer corresponding to the global optimal particle g(t) at the tth iteration, i is the difference with the current iteration number, i=0, 1, ..., 4, $Q_l(t+1)$ represents the number of neurons in the rule layer corresponding to the t+1 iteration of the lth particle.

⑧ If $t < T_{max}$, the number of iterations t increase by 1, and go to step ③; if $t = T_{max}$, stop the training process.

(4) Total Nitrogen Concentration Prediction

Figure 2:
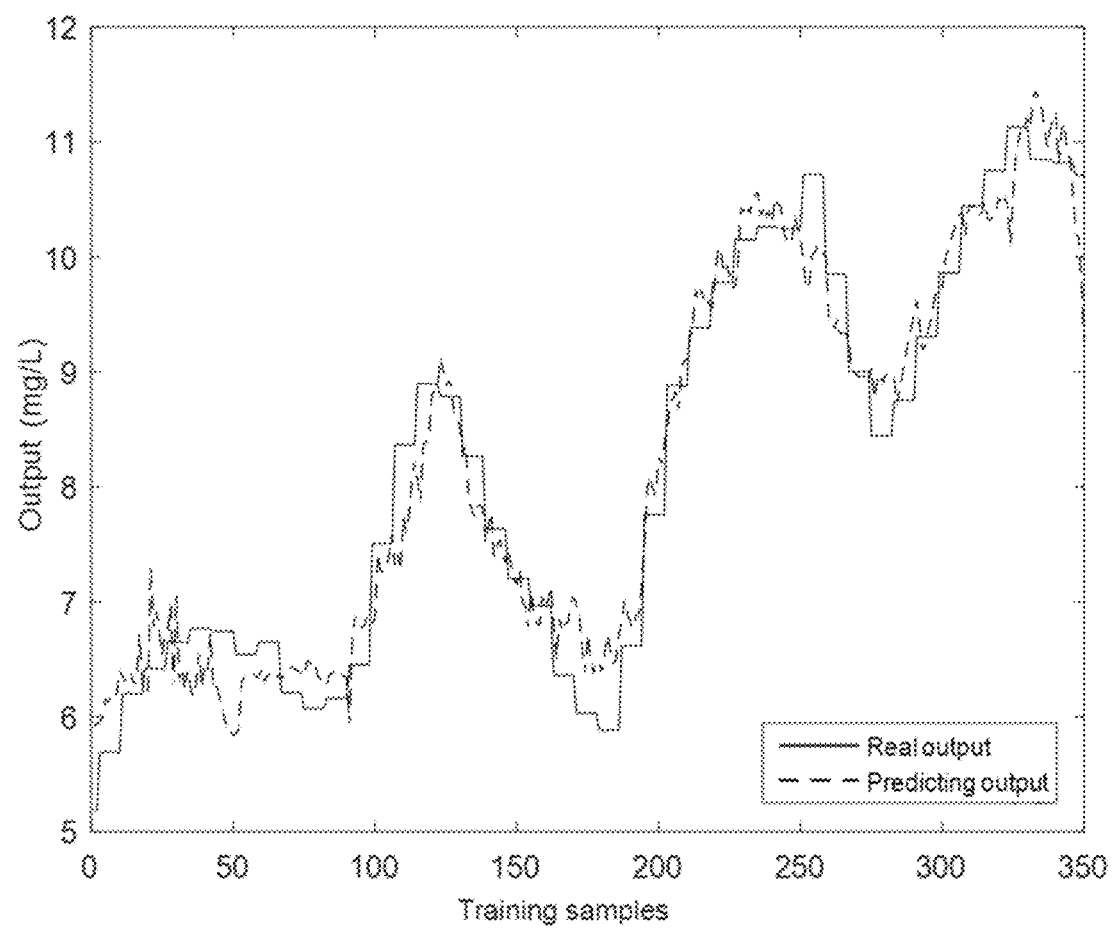
FIG. 2 is a training effect diagram of the total nitrogen intelligent detection method, where the solid line is the actual output value of total nitrogen, and the dotted line is the training value of fuzzy neural network.
Figure 3:
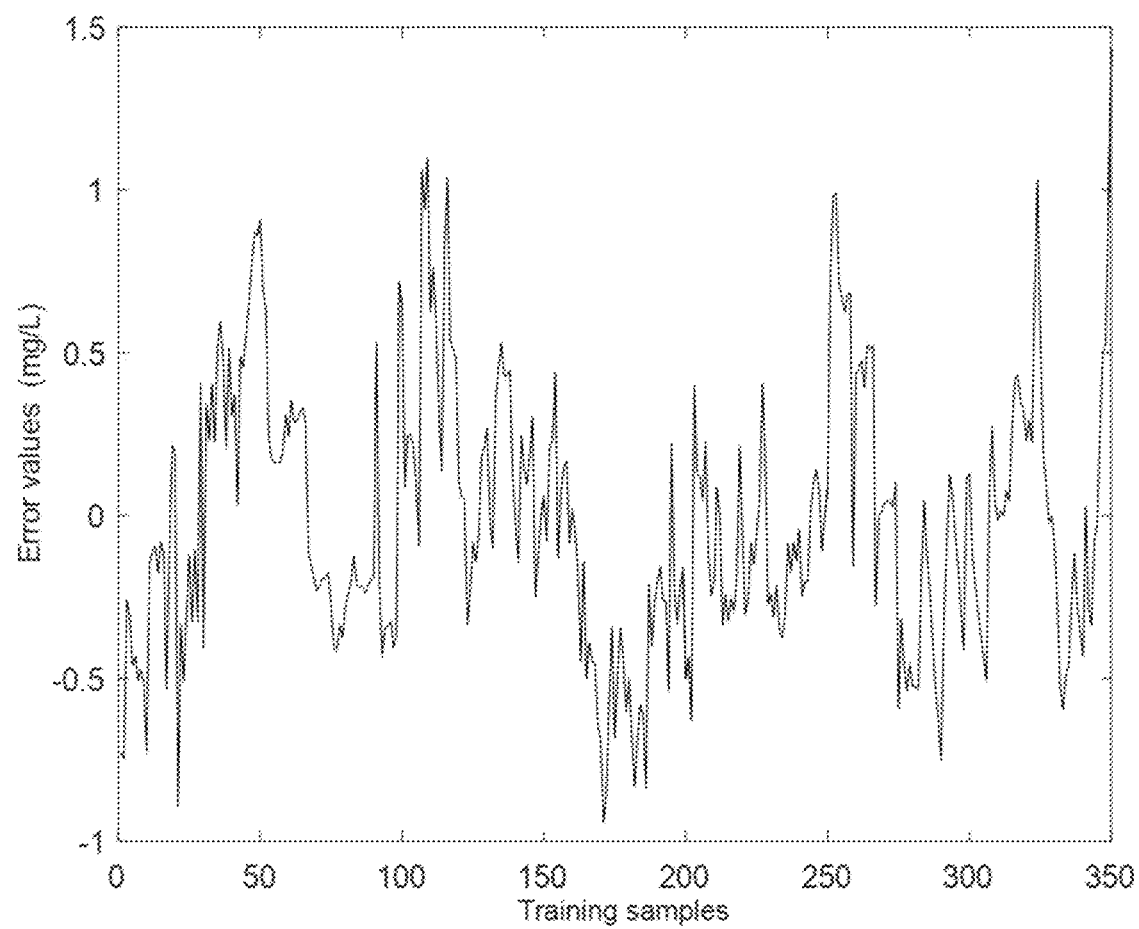
FIG. 3 is a training error diagram of the total nitrogen intelligent detection method.

① The training results of the total nitrogen intelligent detection method are shown in FIG. 2. X-axis: training samples, Y-axis: output, where solid line is the actual output value of total nitrogen and the dotted line is the predicted output value of total nitrogen. FIG. 3 shows the error. X-axis: training samples, Y-axis: error values.

Figure 4:
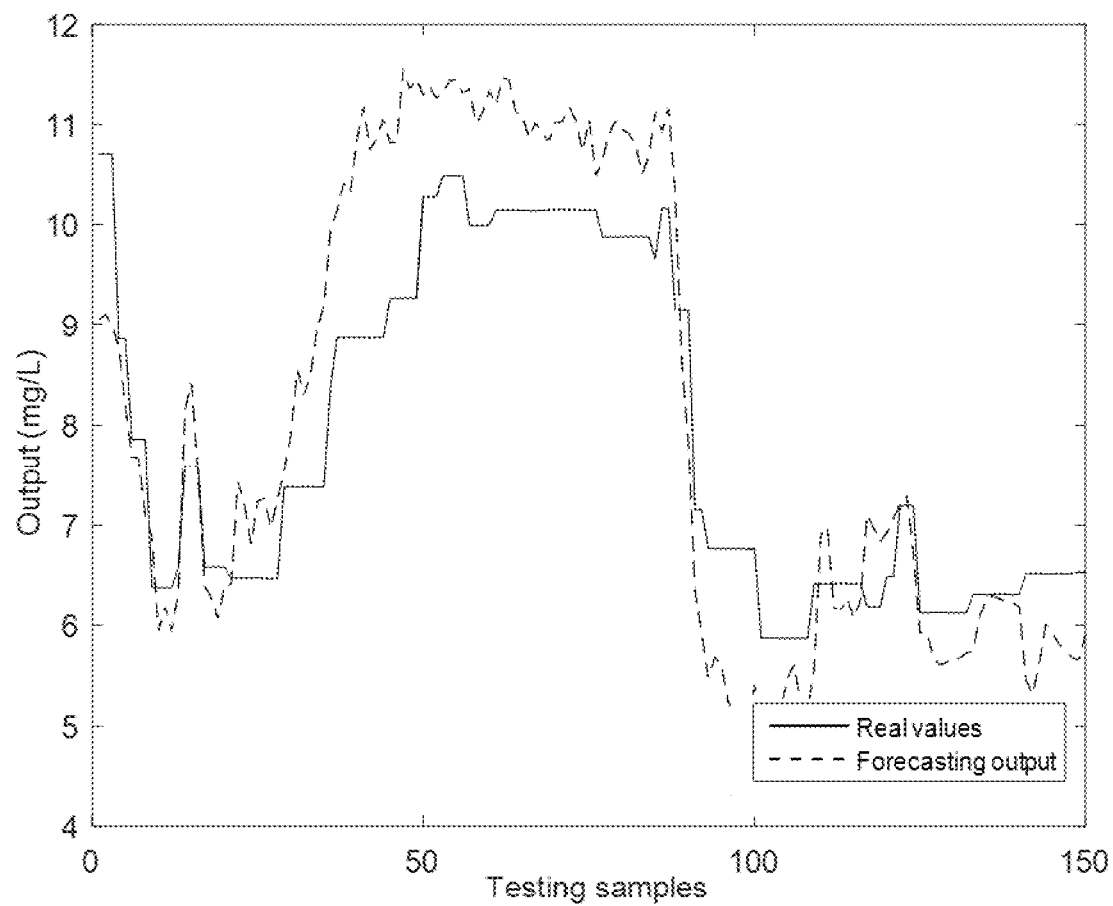
FIG. 4 is the prediction result of the total nitrogen intelligent detection method, where the solid line is the actual output value of total nitrogen, and the dotted line is the predicted value of fuzzy neural network.
Figure 5:
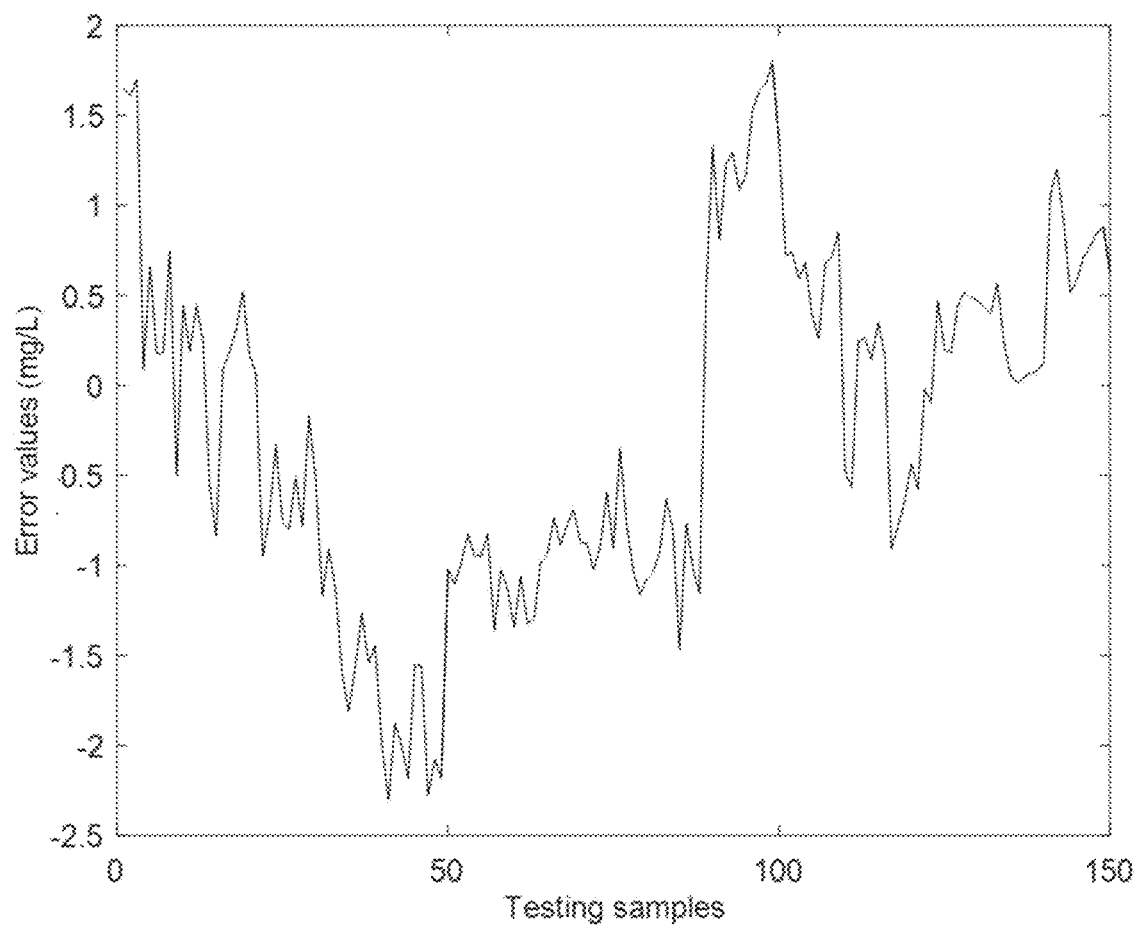
FIG. 5 is the prediction error result of the total nitrogen intelligent detection method.

② The trained total nitrogen intelligent detection model has been detected. The test result of the intelligent detection method is shown in FIG. 4, X-axis: testing samples, Y-axis: output, where the solid line is the actual output value and the dotted line is the predicted output value. The error is shown in FIG. 5, X-axis: testing samples, Y-axis: error values; the experimental results show the effectiveness of the total nitrogen intelligent detection method based on multi-objective optimized fuzzy neural network.

Tables 1-16 show the data in this present disclosure. Training samples and testing samples are provided as follows.

TABLE 1 the training samples of the dosage.

| | | | | | | | | | |
|---|---|---|---|---|---|---|---|---|---|
| 2.38 | 2.38 | 2.38 | 2.38 | 2.38 | 2.38 | 2.38 | 2.38 | 2.38 | 2.38 |
| 2.38 | 2.38 | 2.38 | 2.38 | 2.38 | 2.38 | 2.38 | 2.38 | 2.38 | 2.38 |
| 2.38 | 2.38 | 2.38 | 2.38 | 2.38 | 2.38 | 2.38 | 2.38 | 2.38 | 2.38 |
| 2.38 | 2.38 | 2.38 | 2.38 | 2.38 | 2.38 | 2.23 | 2.23 | 2.23 | 2.23 |
| 2.23 | 2.23 | 2.23 | 2.23 | 2.23 | 2.23 | 2.23 | 2.23 | 2.23 | 2.23 |
| 2.23 | 2.23 | 2.23 | 2.23 | 2.23 | 2.23 | 2.23 | 2.23 | 2.23 | 2.23 |
| 2.23 | 2.23 | 2.23 | 2.23 | 2.23 | 2.23 | 2.23 | 2.23 | 2.23 | 2.23 |
| 2.23 | 2.23 | 2.23 | 2.23 | 2.23 | 2.23 | 2.23 | 2.23 | 2.23 | 2.23 |
| 2.23 | 2.23 | 2.23 | 2.23 | 2.23 | 2.23 | 2.23 | 2.23 | 2.23 | 2.23 |
| 2.23 | 2.23 | 2.23 | 2.23 | 2.23 | 2.23 | 2.23 | 2.23 | 2.23 | 2.23 |
| 2.23 | 2.23 | 2.23 | 2.23 | 2.23 | 2.23 | 2.23 | 2.23 | 2.23 | 2.23 |
| 2.23 | 2.23 | 2.23 | 2.23 | 2.23 | 2.23 | 2.23 | 2.23 | 2.23 | 2.23 |
| 2.23 | 2.23 | 2.18 | 2.18 | 2.18 | 2.18 | 2.18 | 2.18 | 2.18 | 2.18 |
| 2.18 | 2.18 | 2.18 | 2.18 | 2.18 | 2.18 | 2.18 | 2.18 | 2.18 | 2.18 |
| 2.18 | 2.18 | 2.18 | 2.18 | 2.18 | 2.18 | 2.18 | 2.18 | 2.18 | 2.18 |
| 2.18 | 2.18 | 2.18 | 2.18 | 2.18 | 2.18 | 2.18 | 2.18 | 2.18 | 2.18 |
| 2.18 | 2.18 | 2.18 | 2.18 | 2.18 | 2.18 | 2.18 | 2.18 | 2.18 | 2.18 |

TABLE 1-continued the training samples of the dosage.

| | | | | | | | | | |
|---|---|---|---|---|---|---|---|---|---|
| 2.18 | 2.18 | 2.18 | 2.18 | 2.18 | 2.18 | 2.18 | 2.18 | 2.18 | 2.18 |
| 2.18 | 2.18 | 2.18 | 2.18 | 2.18 | 2.18 | 2.18 | 2.18 | 2.18 | 2.18 |
| 2.18 | 2.18 | 2.18 | 2.18 | 2.18 | 2.18 | 2.18 | 2.18 | 2.18 | 2.18 |
| 2.18 | 2.18 | 2.18 | 2.18 | 2.18 | 2.18 | 2.18 | 2.18 | 2.18 | 2.18 |
| 2.18 | 2.18 | 2.18 | 2.18 | 2.18 | 2.18 | 2.18 | 2.18 | 1.09 | 1.09 |
| 1.09 | 1.09 | 1.09 | 1.09 | 1.09 | 1.09 | 1.09 | 1.09 | 1.09 | 1.09 |
| 1.09 | 1.09 | 1.09 | 1.09 | 1.09 | 1.09 | 1.09 | 1.09 | 1.09 | 1.09 |
| 1.09 | 1.09 | 1.09 | 1.09 | 1.09 | 1.09 | 1.09 | 1.09 | 1.09 | 1.09 |
| 1.09 | 1.09 | 1.09 | 1.09 | 1.09 | 1.09 | 1.09 | 1.09 | 1.09 | 1.09 |
| 1.09 | 1.09 | 1.09 | 1.09 | 1.09 | 1.09 | 1.09 | 1.09 | 1.09 | 1.09 |
| 1.09 | 1.09 | 1.09 | 1.09 | 1.09 | 1.09 | 1.09 | 1.09 | 1.09 | 1.09 |
| 1.09 | 1.09 | 1.09 | 1.09 | 1.09 | 1.09 | 1.09 | 1.09 | 1.09 | 1.09 |
| 1.09 | 1.09 | 1.09 | 1.09 | 1.09 | 1.09 | 1.09 | 1.09 | 1.09 | 1.09 |
| 1.09 | 1.09 | 1.09 | 1.09 | 3.06 | 3.06 | 3.06 | 3.06 | 3.06 | 3.06 |
| 3.06 | 3.06 | 3.06 | 3.06 | 3.06 | 3.06 | 3.06 | 3.06 | 3.06 | 3.06 |
| 3.06 | 3.06 | 3.06 | 3.06 | 3.06 | 3.06 | 3.06 | 3.06 | 3.06 | 3.06 |

TABLE 2 the training samples of the oxidation-reduction potential.

| | | | | | | | | | |
|---|---|---|---|---|---|---|---|---|---|
| −217.7 | −224.65 | −230.07 | −235.86 | −240.27 | −245.73 | −250.7 | −256.17 | −261.21 | −264.88 |
| −266.34 | −268.77 | −272.18 | −273.72 | −274.94 | −276.05 | −275.79 | −278.9 | −280.5 | −278 |
| −280.29 | −267.21 | −261.3 | −248.25 | −240.27 | −237.51 | −231.48 | −225.73 | −228.4 | −228.3 |
| −218.55 | −211.46 | −205.71 | −201.33 | −193.82 | −187.67 | −181.9 | −178.22 | −174.31 | −173.3 |
| −169.7 | −167.67 | −165.25 | −167.32 | −166.3 | −170.17 | −173.65 | −174.34 | −179.57 | −191.37 |
| −216.41 | −230.3 | −242.84 | −256.69 | −264.32 | −272.54 | −278.76 | −283.23 | −286.11 | −289.97 |
| −292.11 | −291.52 | −293.53 | −296.56 | −297.74 | −299.25 | −299.2 | −300.83 | −302.48 | −303.49 |
| −304.27 | −307.85 | −308.79 | −311.47 | −310.53 | −307.05 | −311.33 | −312.2 | −317.98 | −319.41 |
| −319.55 | −320.33 | −319.18 | −317.46 | −316.19 | −312.68 | −312.13 | −318.42 | −321.6 | −322.66 |
| −324.43 | −325.8 | −325.8 | −311.47 | −313.22 | −318.14 | −322.47 | −327.23 | −329.26 | −330.22 |
| −329.49 | −329.45 | −330.98 | −334.93 | −337.79 | −338 | −341.37 | −344.19 | −346.05 | −344.33 |
| −341.58 | −339.55 | −341.04 | −334.56 | −335.69 | −339.36 | −345.04 | −345.98 | −350.34 | −351.59 |
| −349.35 | −341.58 | −337.5 | −323.44 | −306.72 | −296.07 | −277.37 | −262.88 | −247.85 | −237.37 |
| −228.16 | −221.45 | −214.03 | −208.73 | −203.55 | −198.2 | −192.73 | −188.94 | −184.23 | −178.58 |
| −175.66 | −172.26 | −169.79 | −167.01 | −164.47 | −163.45 | −160.63 | −159.85 | −156.74 | −154.81 |
| −152.62 | −151.02 | −148.5 | −146.83 | −145.27 | −144.99 | −145.86 | −146.8 | −147.15 | −146.92 |
| −148.12 | −149.75 | −151.42 | −154.72 | −158.46 | −163.08 | −169.79 | −173.94 | −186.26 | −196.2 |
| −211.58 | −219.44 | −227.85 | −235.09 | −241.26 | −246.11 | −247.15 | −246.77 | −242.03 | −243.68 |
| −239.66 | −242.51 | −247.12 | −257.72 | −270.91 | −287.78 | −307.3 | −316.28 | −324.15 | −324.41 |
| −330.79 | −336.21 | −340.56 | −344.47 | −344.59 | −345.63 | −347.65 | −350.74 | −351.71 | −354.11 |
| −354.79 | −355.71 | −358.49 | −359.57 | −362.33 | −363.51 | −365.09 | −367.86 | −371.77 | −376.49 |
| −378.68 | −385.01 | −388.9 | −392.69 | −393.82 | −390.01 | −392.2 | −386.94 | −392.13 | −394.76 |
| −395.12 | −393.42 | −387.04 | −393.4 | −391.4 | −386.71 | −385.04 | −388.52 | −396.81 | −400.39 |
| −399.31 | −399.22 | −402.21 | −403.53 | −404.87 | −402.35 | −407.04 | −409.13 | −408 | −409.06 |
| −409.96 | −409.72 | −409.42 | −395.26 | −393.92 | −380.14 | −384 | −386.47 | −372.22 | −341.62 |
| −314.91 | −291.36 | −273.5 | −258.9 | −247.45 | −238.48 | −230.66 | −223.5 | −215.06 | −208.07 |
| −201 | −193.72 | −185.81 | −179.99 | −173.61 | −168.59 | −162.72 | −158.27 | −155.89 | −151.44 |
| −150.43 | −148.36 | −146.59 | −144.33 | −147.11 | −147.51 | −144.54 | −141.15 | −136.93 | −139.48 |
| −138.86 | −141.95 | −144.38 | −146.05 | −149.13 | −155.26 | −169.67 | −184.8 | −194.29 | −211.18 |
| −224.11 | −239.23 | −249.12 | −259.79 | −274.47 | −290.65 | −314.94 | −336.65 | −338.87 | −350.1 |
| −356.56 | −363.18 | −364 | −368.74 | −370.2 | −374.72 | −378.37 | −390.57 | −397.54 | −403.22 |
| −403.01 | −404.12 | −405.27 | −407.84 | −397.43 | −405.08 | −404.28 | −389.21 | −402.11 | −397.03 |
| −400.51 | −395.45 | −390.38 | −376.7 | −374.74 | −378.09 | −388.66 | −398.96 | −400.04 | −405.76 |
| −400.84 | −404.75 | −407.81 | −408.59 | −410.45 | −397.73 | −402.8 | −410.99 | −410.99 | −406.38 |
| −383.48 | −398.02 | −401.08 | −398.04 | −389.63 | −375.87 | −365.06 | −340.54 | −336.77 | −306.69 |

TABLE 3 the training samples of the orthophosphate.

| | | | | | | | | | |
|---|---|---|---|---|---|---|---|---|---|
| 0.636 | 0.6359 | 0.636 | 0.636 | 0.6181 | 0.6181 | 0.5753 | 0.5753 | 0.5471 | 0.5471 |
| 0.529 | 0.5289 | 0.5109 | 0.5109 | 0.4983 | 0.4983 | 0.4834 | 0.4833 | 0.4833 | 0.407 |
| 0.407 | 0.4335 | 0.4335 | 0.4098 | 0.4098 | 0.3902 | 0.3902 | 0.3742 | 0.3743 | 0.3652 |
| 0.3651 | 0.346 | 0.3459 | 0.316 | 0.3159 | 0.3211 | 0.321 | 0.343 | 0.343 | 0.3541 |
| 0.3541 | 0.361 | 0.3611 | 0.3583 | 0.3583 | 0.3402 | 0.3401 | 0.338 | 0.3381 | 0.3272 |
| 0.3273 | 0.3374 | 0.3373 | 0.346 | 0.346 | 0.3408 | 0.3407 | 0.3324 | 0.3324 | 0.3592 |
| 0.3592 | 0.3857 | 0.3857 | 0.3672 | 0.3672 | 0.4216 | 0.4216 | 0.439 | 0.439 | 0.4651 |
| 0.4651 | 0.4505 | 0.4505 | 0.4393 | 0.4394 | 0.4435 | 0.4435 | 0.4222 | 0.4223 | 0.3809 |
| 0.3808 | 0.346 | 0.3461 | 0.3245 | 0.3245 | 0.3057 | 0.3057 | 0.2799 | 0.28 | 0.2771 |
| 0.259 | 0.2591 | 0.2615 | 0.2615 | 0.2541 | 0.2543 | 0.2605 | 0.2605 | 0.2721 | 0.272 |
| 0.2804 | 0.2805 | 0.2948 | 0.2948 | 0.3066 | 0.3066 | 0.3123 | 0.3123 | 0.327 | 0.3269 |
| 0.3315 | 0.3315 | 0.348 | 0.3479 | 0.3462 | 0.3462 | 0.3299 | 0.3298 | 0.303 | 0.303 |
| 0.2908 | 0.2908 | 0.2818 | 0.2818 | 0.272 | 0.272 | 0.263 | 0.2629 | 0.2654 | 0.2653 |
| 0.2695 | 0.2695 | 0.2643 | 0.2643 | 0.234 | 0.234 | 0.2266 | 0.2266 | 0.2176 | 0.2176 |
| 0.2099 | 0.21 | 0.2074 | 0.2074 | 0.2011 | 0.2012 | 0.1875 | 0.1875 | 0.1962 | 0.1962 |
| 0.1976 | 0.1976 | 0.1916 | 0.1916 | 0.1927 | 0.1927 | 0.1913 | 0.1913 | 0.1821 | 0.1822 |
| 0.194 | 0.194 | 0.2013 | 0.2013 | 0.2097 | 0.2097 | 0.2184 | 0.2184 | 0.2079 | 0.2079 |
| 0.2124 | 0.2124 | 0.22 | 0.2201 | 0.2322 | 0.2322 | 0.2249 | 0.2249 | 0.2249 | 0.1842 |
| 0.233 | 0.233 | 0.2312 | 0.2312 | 0.2183 | 0.2183 | 0.2187 | 0.2188 | 0.2337 | 0.2337 |
| 0.2355 | 0.2354 | 0.2351 | 0.2351 | 0.256 | 0.256 | 0.2606 | 0.2606 | 0.2773 | 0.2774 |
| 0.2924 | 0.2923 | 0.2885 | 0.2886 | 0.3046 | 0.3047 | 0.2973 | 0.2973 | 0.305 | 0.305 |
| 0.3106 | 0.3105 | 0.3106 | 0.3106 | 0.3138 | 0.3138 | 0.3107 | 0.3106 | 0.3019 | 0.3019 |
| 0.2935 | 0.2935 | 0.3044 | 0.3043 | 0.2643 | 0.2643 | 0.3009 | 0.3009 | 0.2988 | 0.2988 |
| 0.3082 | 0.3082 | 0.3187 | 0.3187 | 0.3041 | 0.3041 | 0.2964 | 0.2963 | 0.2869 | 0.2869 |
| 0.2962 | 0.2962 | 0.2941 | 0.2941 | 0.29 | 0.2899 | 0.2917 | 0.2917 | 0.2917 | 0.2917 |
| 0.2983 | 0.2983 | 0.3091 | 0.3147 | 0.322 | 0.329 | 0.3161 | 0.3028 | 0.3178 | 0.3251 |
| 0.3185 | 0.3053 | 0.3036 | 0.2997 | 0.2966 | 0.2904 | 0.2903 | 0.258 | 0.2579 | 0.2328 |
| 0.2328 | 0.2286 | 0.2287 | 0.217 | 0.2171 | 0.2081 | 0.208 | 0.2045 | 0.2045 | 0.209 |
| 0.209 | 0.2331 | 0.2195 | 0.2195 | 0.2303 | 0.2304 | 0.2244 | 0.2244 | 0.2147 | 0.2147 |
| 0.2404 | 0.2404 | 0.2401 | 0.2402 | 0.2443 | 0.2443 | 0.2475 | 0.2475 | 0.2607 | 0.2607 |
| 0.2471 | 0.2472 | 0.2583 | 0.2583 | 0.2562 | 0.2562 | 0.2621 | 0.2622 | 0.2583 | 0.2583 |
| 0.2506 | 0.2507 | 0.2454 | 0.2454 | 0.2402 | 0.2402 | 0.2399 | 0.2398 | 0.2426 | 0.2426 |
| 0.2374 | 0.2374 | 0.2332 | 0.2333 | 0.2357 | 0.2357 | 0.2182 | 0.2182 | 0.2183 | 0.2183 |
| 0.2246 | 0.2246 | 0.2211 | 0.2211 | 0.2243 | 0.2243 | 0.2173 | 0.2173 | 0.2086 | 0.2086 |
| 0.2071 | 0.2071 | 0.2043 | 0.2043 | 0.2157 | 0.2157 | 0.2202 | 0.2202 | 0.2441 | 0.2441 |

TABLE 4 the training samples of the pH value.

| | | | | | | | | | |
|---|---|---|---|---|---|---|---|---|---|
| 7.78 | 7.69 | 7.57 | 7.62 | 7.6 | 7.53 | 7.44 | 7.38 | 7.34 | 7.32 |
| 7.3 | 7.6 | 7.61 | 7.58 | 7.54 | 7.51 | 7.46 | 7.42 | 7.38 | 7.63 |
| 7.63 | 7.61 | 7.58 | 7.55 | 7.51 | 7.47 | 7.44 | 7.59 | 7.35 | 7.43 |
| 7.46 | 7.42 | 7.37 | 7.32 | 7.28 | 7.36 | 7.38 | 7.43 | 7.48 | 7.51 |
| 7.53 | 7.57 | 7.59 | 7.62 | 7.65 | 7.76 | 7.83 | 7.88 | 7.88 | 7.86 |
| 7.84 | 7.87 | 7.95 | 7.97 | 7.96 | 7.93 | 7.91 | 7.88 | 7.87 | 7.89 |
| 7.93 | 7.98 | 7.98 | 7.97 | 7.95 | 7.93 | 7.92 | 7.95 | 7.98 | 7.97 |
| 7.96 | 7.95 | 7.94 | 7.93 | 7.92 | 8.1 | 8.21 | 8.18 | 8.16 | 8.13 |
| 8.1 | 8.09 | 8.07 | 8.2 | 8.21 | 8.22 | 8.22 | 8.21 | 8.18 | 8.17 |
| 8.15 | 8.38 | 8.4 | 8.37 | 8.34 | 8.29 | 8.25 | 8.21 | 8.18 | 8.17 |
| 8.45 | 8.5 | 8.45 | 8.38 | 8.31 | 8.26 | 8.23 | 8.2 | 8.15 | 8.25 |
| 8.34 | 8.35 | 8.32 | 8.27 | 8.23 | 8.21 | 8.19 | 8.17 | 8.16 | 8.14 |
| 8.12 | 8.11 | 8.09 | 8.09 | 8.15 | 8.27 | 8.32 | 8.31 | 8.27 | 8.24 |
| 8.21 | 8.2 | 8.19 | 8.18 | 8.16 | 8.15 | 8.14 | 8.13 | 8.12 | 8.13 |
| 8.11 | 8.08 | 8.06 | 8.06 | 8.05 | 8.05 | 8.04 | 8.05 | 8.05 | 8.05 |
| 8.04 | 8.05 | 8.06 | 8.07 | 8.07 | 8.07 | 8.08 | 8.08 | 8.09 | 8.09 |
| 8.08 | 8.08 | 8.07 | 8.07 | 8.07 | 8.07 | 8.07 | 8.07 | 8.07 | 8.07 |
| 8.07 | 8.08 | 8.08 | 8.08 | 8.09 | 8.09 | 8.09 | 8.09 | 8.09 | 8.09 |
| 8.09 | 8.1 | 8.1 | 8.09 | 8.09 | 8.09 | 8.21 | 8.1 | 8.01 | 7.87 |
| 7.77 | 7.71 | 7.67 | 7.64 | 7.62 | 7.82 | 7.71 | 7.66 | 7.61 | 7.55 |
| 7.52 | 7.51 | 7.51 | 7.59 | 7.56 | 7.5 | 7.45 | 7.42 | 7.39 | 7.38 |
| 7.37 | 7.53 | 7.5 | 7.43 | 7.37 | 7.34 | 7.31 | 7.29 | 7.28 | 7.48 |
| 7.48 | 7.46 | 7.39 | 7.35 | 7.32 | 7.3 | 7.3 | 7.52 | 7.53 | 7.5 |
| 7.44 | 7.4 | 7.38 | 7.37 | 7.37 | 7.53 | 7.56 | 7.53 | 7.49 | 7.46 |
| 7.44 | 7.45 | 7.46 | 7.6 | 7.61 | 7.55 | 7.48 | 7.45 | 7.42 | 7.42 |
| 7.42 | 7.44 | 7.35 | 7.24 | 7.16 | 7.12 | 7.1 | 7.09 | 7.1 | 7.35 |
| 7.39 | 7.36 | 7.33 | 7.29 | 7.28 | 7.28 | 7.29 | 7.46 | 7.47 | 7.42 |
| 7.39 | 7.37 | 7.37 | 7.38 | 7.38 | 7.56 | 7.55 | 7.46 | 7.39 | 7.35 |
| 7.34 | 7.34 | 7.33 | 7.57 | 7.55 | 7.48 | 7.4 | 7.33 | 7.28 | 7.25 |
| 7.24 | 7.54 | 7.61 | 7.61 | 7.58 | 7.56 | 7.54 | 7.53 | 7.53 | 7.7 |
| 7.62 | 7.55 | 7.47 | 7.4 | 7.33 | 7.28 | 7.24 | 7.55 | 7.55 | 7.51 |
| 7.46 | 7.43 | 7.38 | 7.33 | 7.29 | 7.51 | 7.48 | 7.45 | 7.42 | 7.38 |
| 7.32 | 7.28 | 7.26 | 7.48 | 7.52 | 7.5 | 7.48 | 7.47 | 7.44 | 7.41 |
| 7.39 | 7.48 | 7.48 | 7.44 | 7.4 | 7.37 | 7.32 | 7.28 | 7.26 | 7.4 |
| 7.42 | 7.4 | 7.38 | 7.36 | 7.32 | 7.29 | 7.28 | 7.37 | 7.35 | 7.33 |

TABLE 5 the training samples of the ammonia nitrogen.

| | | | | | | | | | |
|---|---|---|---|---|---|---|---|---|---|
| 74.82 | 74.82 | 74.8 | 74.82 | 71.61 | 71.61 | 71.61 | 71.61 | 71.61 | 71.61 |
| 71.61 | 71.61 | 76.42 | 76.42 | 76.42 | 76.42 | 76.42 | 76.42 | 76.42 | 76.42 |
| 68.64 | 68.64 | 68.63 | 68.63 | 68.63 | 68.63 | 68.63 | 68.63 | 74.79 | 74.79 |
| 74.79 | 74.79 | 74.79 | 74.79 | 74.79 | 74.79 | 73.14 | 73.14 | 73.14 | 73.14 |
| 73.14 | 73.14 | 73.14 | 73.14 | 76.42 | 76.42 | 76.42 | 76.4 | 76.42 | 76.4 |
| 76.4 | 76.4 | 65.78 | 65.78 | 65.78 | 65.78 | 65.71 | 65.71 | 65.78 | 65.78 |
| 71.59 | 71.59 | 71.58 | 71.58 | 71.59 | 71.59 | 71.58 | 71.58 | 71.59 | 71.58 |
| 71.58 | 71.57 | 71.59 | 71.58 | 71.59 | 71.59 | 76.4 | 76.42 | 76.42 | 76.42 |
| 76.42 | 76.42 | 76.42 | 76.42 | 76.42 | 76.42 | 76.43 | 76.43 | 76.43 | 76.43 |
| 76.43 | 76.43 | 68.65 | 68.65 | 68.65 | 68.65 | 68.65 | 68.65 | 68.65 | 68.65 |
| 68.65 | 68.65 | 68.64 | 68.64 | 68.65 | 68.64 | 68.64 | 68.64 | 70.14 | 70.14 |

TABLE 5-continued

| | the training samples of the ammonia nitrogen. |
|---|---|---|---|---|---|---|---|---|---|
| 70.14 | 70.14 | 70.14 | 70.14 | 70.14 | 70.14 | 63.05 | 63.05 | 63.04 | 63.04 |
| 63.04 | 63.04 | 63.04 | 63.01 | 64.38 | 64.37 | 64.39 | 64.37 | 64.37 | 64.37 |
| 64.34 | 64.37 | 74.8 | 74.79 | 74.79 | 74.79 | 74.79 | 74.79 | 74.79 | 74.78 |
| 70.07 | 70.07 | 70.07 | 70.07 | 70.04 | 70.17 | 70.06 | 70.02 | 70.14 | 70.15 |
| 70.04 | 70.03 | 70.15 | 70.17 | 70.04 | 70.07 | 67.16 | 67.16 | 67.15 | 67.16 |
| 67.17 | 67.16 | 67.14 | 67.17 | 57.95 | 57.95 | 57.93 | 57.95 | 57.95 | 57.93 |
| 57.95 | 57.95 | 73.22 | 73.22 | 73.22 | 73.22 | 73.22 | 73.22 | 73.22 | 73.22 |
| 71.61 | 71.61 | 71.61 | 71.61 | 71.61 | 71.61 | 71.61 | 61.74 | 67.17 | 67.17 |
| 67.17 | 67.17 | 67.17 | 67.17 | 67.17 | 67.17 | 57.96 | 57.96 | 57.96 | 57.96 |
| 57.95 | 57.95 | 57.96 | 57.95 | 60.46 | 60.45 | 60.45 | 60.47 | 60.45 | 60.45 |
| 60.45 | 60.45 | 60.45 | 60.45 | 60.45 | 60.45 | 60.45 | 60.45 | 60.45 | 60.45 |
| 53.31 | 53.31 | 53.31 | 53.31 | 53.29 | 53.31 | 53.31 | 53.29 | 61.73 | 61.73 |
| 61.73 | 61.73 | 61.73 | 61.73 | 61.73 | 61.73 | 61.73 | 61.73 | 61.72 | 61.74 |
| 61.73 | 61.72 | 61.72 | 61.71 | 59.25 | 59.24 | 59.12 | 59.19 | 59.18 | 59.19 |
| 59.2 | 59.21 | 57.96 | 57.92 | 57.93 | 57.93 | 57.98 | 57.95 | 57.93 | 57.95 |
| 60.31 | 60.46 | 60.42 | 60.45 | 60.45 | 60.45 | 60.45 | 60.46 | 60.47 | 60.46 |
| 60.45 | 60.47 | 60.46 | 60.46 | 60.46 | 60.46 | 57.96 | 57.97 | 57.95 | 57.99 |
| 57.96 | 57.96 | 57.96 | 57.97 | 48.01 | 48.02 | 47.97 | 48 | 48.01 | 48.02 |
| 48.12 | 48.01 | 10.44 | 10.43 | 10.46 | 10.44 | 10.42 | 10.42 | 10.42 | 10.43 |
| 19.64 | 19.64 | 19.64 | 19.64 | 19.66 | 19.56 | 19.56 | 19.56 | 25.63 | 25.63 |
| 25.63 | 25.63 | 25.63 | 25.63 | 25.62 | 25.62 | 43.27 | 43.27 | 43.27 | 43.27 |
| 43.27 | 43.27 | 43.27 | 43.27 | 41.49 | 41.49 | 41.49 | 41.49 | 41.49 | 41.49 |
| 41.49 | 41.49 | 42.34 | 42.34 | 42.34 | 42.34 | 42.34 | 42.34 | 42.34 | 42.34 |
| 44.15 | 44.15 | 44.15 | 44.15 | 44.16 | 44.15 | 44.15 | 44.15 | 50.02 | 50.05 |

TABLE 6

| | the training samples of the nitrate nitrogen. |
|---|---|---|---|---|---|---|---|---|---|
| 2.79 | 3.15 | 3.4 | 3.48 | 3.59 | 3.52 | 3.81 | 3.72 | 3.84 | 4.3 |
| 4.17 | 3.83 | 4.2 | 4.35 | 4.23 | 4.31 | 4.98 | 4.38 | 4.22 | 4.13 |
| 4.89 | 4.33 | 4.6 | 4.49 | 4.3 | 4.64 | 4.7 | 4.93 | 4.5 | 5.38 |
| 4.81 | 5.09 | 4.92 | 5.32 | 5.16 | 4.96 | 4.9 | 5.2 | 4.65 | 4.93 |
| 4.81 | 5.28 | 4.47 | 4.49 | 4.5 | 4.15 | 3.62 | 2.5 | 2.41 | 1.8 |
| 1.18 | 1.2 | 1.02 | 0.93 | 1.03 | 1.24 | 1.25 | 1.03 | 1.01 | 1.11 |
| 1.37 | 1.32 | 1.22 | 1.28 | 1.36 | 1.51 | 1 | 0.92 | 1.24 | 1.43 |
| 1.29 | 1.21 | 1.25 | 1.19 | 0.92 | 0.79 | 1.15 | 0.84 | 1.3 | 1.11 |
| 1.05 | 1.43 | 1.8 | 1.4 | 1.12 | 1.14 | 1.27 | 1.49 | 1.08 | 1.4 |
| 1.25 | 1.51 | 1.18 | 1.44 | 2.27 | 2.49 | 3.22 | 3.25 | 3.19 | 3.49 |
| 4.01 | 3.44 | 3.53 | 3.77 | 4.06 | 4.42 | 3.95 | 4.19 | 4.03 | 4.58 |
| 4.35 | 4.52 | 4.81 | 4.96 | 5.05 | 4.8 | 5.12 | 5.15 | 5.17 | 5.55 |
| 5.65 | 5.77 | 6.19 | 6.28 | 6.32 | 6.47 | 6.62 | 6.33 | 6.55 | 6.63 |
| 6.24 | 6.55 | 6.38 | 6.24 | 6.23 | 6.51 | 6.62 | 6.63 | 6.06 | 6.32 |
| 6.31 | 5.72 | 5.91 | 6.01 | 5.9 | 5.74 | 5.98 | 5.77 | 5.6 | 5.52 |
| 5.72 | 5.32 | 5.31 | 5.01 | 5.46 | 5.2 | 4.96 | 4.92 | 5.29 | 5.15 |
| 5.22 | 5.39 | 4.94 | 4.46 | 4.62 | 4.41 | 4.46 | 4.46 | 4.75 | 4.77 |
| 4.59 | 4.38 | 4.6 | 4.16 | 4.64 | 4.28 | 4.06 | 4.27 | 4.33 | 4.35 |

TABLE 6-continued

| | the training samples of the nitrate nitrogen. |
|---|---|---|---|---|---|---|---|---|---|
| 4.34 | 4.54 | 4.28 | 4 | 4.01 | 4.25 | 3.98 | 3.9 | 3.99 | 4.1 |
| 4.09 | 4.27 | 4.27 | 4.62 | 4.98 | 5.25 | 5.12 | 5.01 | 4.94 | 5.31 |
| 5.22 | 5.42 | 5.5 | 5.71 | 5.77 | 5.89 | 5.72 | 6.13 | 6.24 | 6.12 |
| 6.39 | 6.17 | 6.7 | 6.5 | 6.8 | 6.83 | 7.14 | 7.02 | 6.71 | 7.47 |
| 7.13 | 7.16 | 7.38 | 7 | 7.19 | 7.33 | 7.34 | 7.48 | 6.87 | 7.48 |
| 7.36 | 7.9 | 7.63 | 7.58 | 7.25 | 7.69 | 7.27 | 7.82 | 7.58 | 8.04 |
| 7.4 | 7.61 | 7.62 | 7.67 | 8.01 | 7.92 | 8.03 | 7.5 | 7.64 | 5.94 |
| 5.38 | 4.64 | 4.14 | 4.39 | 3.83 | 4.02 | 3.7 | 4.17 | 4.33 | 4.14 |
| 4.29 | 4.24 | 4.89 | 4.76 | 5.36 | 5.91 | 5.61 | 5.79 | 6.27 | 6.15 |
| 5.44 | 5.45 | 5.9 | 5.51 | 5.12 | 5.98 | 6.66 | 6.58 | 6.59 | 6.29 |
| 5.91 | 5.23 | 5.57 | 5.34 | 5.45 | 5.54 | 5.56 | 5.46 | 5.68 | 6.11 |
| 5.52 | 5.69 | 5.56 | 5.69 | 6.12 | 6.47 | 6.32 | 6.17 | 6.9 | 6.56 |
| 6.42 | 6.71 | 6.6 | 6.86 | 6.94 | 6.97 | 7.51 | 7.56 | 7.02 | 7.12 |
| 7.46 | 7.53 | 7.99 | 8.12 | 7.69 | 7.77 | 8.13 | 7.53 | 7.89 | 7.45 |
| 7.99 | 7.71 | 7.88 | 8.06 | 8.09 | 7.58 | 7.7 | 7.8 | 7.81 | 7.77 |
| 7.74 | 7.52 | 7.42 | 7.68 | 7.72 | 7.56 | 7.9 | 7.79 | 7.61 | 7.66 |
| 7.75 | 7.57 | 7.5 | 7.88 | 7.59 | 7.63 | 7.91 | 7.47 | 7.91 | 7.99 |

TABLE 7

| | the training samples of the chemical oxygen demand. |
|---|---|---|---|---|---|---|---|---|---|
| 198.51 | 200.68 | 204.59 | 207.84 | 210.55 | 212.59 | 221.26 | 223.01 | 222.68 | 223.65 |
| 218.79 | 215.21 | 212.49 | 208.37 | 207.95 | 206.75 | 209.35 | 214.99 | 220.72 | 100.93 |
| 42.96 | 42.85 | 43.83 | 41.99 | 43.17 | 42.53 | 41.22 | 42.51 | 42.74 | 43.82 |
| 247.68 | 245.3 | 243.46 | 243.57 | 242.16 | 243.47 | 244.22 | 246.28 | 249.21 | 250.07 |
| 252.98 | 254.73 | 256.03 | 256.78 | 256.89 | 257.64 | 258.41 | 258.62 | 257.54 | 254.61 |
| 252.23 | 248.87 | 247.36 | 247.56 | 247.45 | 247.35 | 245.18 | 243.56 | 243.67 | 243.56 |
| 243.78 | 242.9 | 240.41 | 237.17 | 234.35 | 229.8 | 227.53 | 225.04 | 222.65 | 221.36 |
| 219.52 | 219.3 | 219.08 | 215.95 | 214.1 | 211.53 | 211.61 | 210 | 209.46 | 207.83 |
| 208.59 | 209.89 | 212.71 | 216.06 | 219.85 | 226.24 | 231.44 | 233.02 | 234.47 | 236.75 |
| 115.67 | 247.05 | 243.8 | 243.24 | 245.19 | 249.53 | 248.76 | 244.34 | 238.38 | 234.37 |
| 231.99 | 232.64 | 233.83 | 241.31 | 250.4 | 252.36 | 251.05 | 248.78 | 249.33 | 252.59 |
| 190.28 | 110.13 | 110.45 | 39.39 | 177.06 | 244.22 | 243.46 | 246.92 | 257.32 | 263.6 |
| 258.95 | 253.42 | 257.97 | 257.64 | 252.99 | 252.22 | 249.95 | 247.15 | 247.35 | 235.76 |
| 168.49 | 231.74 | 233.69 | 233.92 | 235.43 | 235.32 | 234.99 | 235.11 | 239.13 | 245.52 |
| 247.15 | 249.21 | 246.92 | 245.53 | 244.65 | 244.12 | 242.81 | 241.83 | 239.68 | 239.56 |
| 238.59 | 236.75 | 235.56 | 234.25 | 233.38 | 232.62 | 232.51 | 231.44 | 231.33 | 228.93 |
| 227.76 | 225.49 | 223.75 | 223.32 | 221.91 | 222.45 | 222.13 | 222.14 | 220.94 | 219.32 |
| 217.81 | 219.97 | 220.08 | 218.34 | 217.05 | 215.54 | 211.42 | 204.05 | 201.02 | 202.2 |
| 203.95 | 206.88 | 209.25 | 213.36 | 219.1 | 228.09 | 232.75 | 233.73 | 232.1 | 234.38 |
| 234.5 | 236.32 | 236.65 | 236.01 | 237.2 | 237.43 | 238.83 | 239.91 | 240.03 | 238.83 |
| 240.89 | 243.93 | 246.52 | 249.11 | 246.74 | 244.25 | 242.63 | 243.38 | 245.97 | 248.69 |
| 251.81 | 253.78 | 255.18 | 255.06 | 251.16 | 245.86 | 244.24 | 242.72 | 241.19 | 243.58 |

TABLE 7-continued the training samples of the chemical oxygen demand.

| | | | | | | | | | |
|---|---|---|---|---|---|---|---|---|---|
| 245.2 | 245.31 | 246.29 | 248.24 | 250.4 | 253.32 | 254.08 | 254.19 | 253.54 | 254.62 |
| 254.19 | 251.91 | 252.02 | 253.43 | 254.95 | 257.33 | 259.71 | 261.88 | 263.51 | 263.4 |
| 261.11 | 259.17 | 257.65 | 257.21 | 255.59 | 252.12 | 246.38 | 239.45 | 233.38 | 230.13 |
| 231.1 | 231.54 | 229.59 | 104.28 | 41.45 | 40.03 | 41.02 | 40.68 | 108.38 | 228.73 |
| 165.69 | 165.69 | 108.41 | 227.21 | 226.7 | 224.83 | 224.52 | 224.07 | 223.55 | 227.13 |
| 226.34 | 227.53 | 226.34 | 227.45 | 106.34 | 228.53 | 102.22 | 38.95 | 222.23 | 220.2 |
| 224.63 | 236.43 | 255.28 | 259.97 | 254.53 | 246.95 | 241.32 | 240.34 | 238.71 | 238.82 |
| 239.7 | 240.12 | 241 | 242.72 | 243.49 | 247.27 | 258.11 | 263.11 | 261.46 | 258.75 |
| 257.24 | 258.11 | 261.46 | 261.46 | 260.28 | 259.31 | 257.46 | 258.54 | 257.68 | 257.03 |
| 255.29 | 254.85 | 250.74 | 245.11 | 241.1 | 241.32 | 239.47 | 240.55 | 246.19 | 249.34 |
| 250.08 | 251.93 | 252.26 | 253.02 | 251.81 | 251.38 | 253.23 | 253.65 | 254.76 | 255.72 |
| 257.23 | 258.42 | 259.83 | 260.37 | 260.15 | 257.99 | 257.67 | 255.06 | 254.84 | 255.06 |
| 252.58 | 250.95 | 249.65 | 245.86 | 242.83 | 239.89 | 238.26 | 231.44 | 225.16 | 221.59 |

TABLE 8 the training samples of the total nitrogen.

| | | | | | | | | | |
|---|---|---|---|---|---|---|---|---|---|
| 5.188 | 5.188 | 5.691 | 5.693 | 5.695 | 5.697 | 5.691 | 5.698 | 5.689 | 5.686 |
| 6.201 | 6.202 | 6.207 | 6.2 | 6.202 | 6.199 | 6.2 | 6.207 | 6.423 | 6.423 |
| 6.42 | 6.421 | 6.417 | 6.42 | 6.415 | 6.413 | 6.653 | 6.654 | 6.653 | 6.653 |
| 6.648 | 6.653 | 6.643 | 6.647 | 6.77 | 6.766 | 6.767 | 6.771 | 6.772 | 6.765 |
| 6.77 | 6.767 | 6.746 | 6.743 | 6.743 | 6.742 | 6.746 | 6.746 | 6.738 | 6.747 |
| 6.542 | 6.538 | 6.543 | 6.538 | 6.541 | 6.542 | 6.539 | 6.539 | 6.653 | 6.649 |
| 6.649 | 6.649 | 6.651 | 6.649 | 6.647 | 6.652 | 6.21 | 6.207 | 6.21 | 6.209 |
| 6.208 | 6.214 | 6.211 | 6.21 | 6.071 | 6.07 | 6.071 | 6.073 | 6.068 | 6.068 |
| 6.074 | 6.074 | 6.157 | 6.16 | 6.162 | 6.157 | 6.162 | 6.161 | 6.157 | 6.163 |
| 6.45 | 6.452 | 6.448 | 6.454 | 6.451 | 6.453 | 6.451 | 6.453 | 7.507 | 7.507 |
| 7.509 | 7.506 | 7.507 | 7.51 | 7.507 | 7.504 | 8.364 | 8.366 | 8.366 | 8.366 |
| 8.361 | 8.364 | 8.361 | 8.365 | 8.899 | 8.898 | 8.899 | 8.897 | 8.9 | 8.894 |
| 8.892 | 8.899 | 8.784 | 8.788 | 8.788 | 8.784 | 8.783 | 8.787 | 8.786 | 8.783 |
| 8.268 | 8.265 | 8.267 | 8.267 | 8.264 | 8.266 | 8.266 | 8.264 | 7.638 | 7.635 |
| 7.636 | 7.636 | 7.635 | 7.635 | 7.632 | 7.634 | 7.205 | 7.201 | 7.203 | 7.203 |
| 7.201 | 7.205 | 7.203 | 7.203 | 6.963 | 6.968 | 6.969 | 6.963 | 6.965 | 6.964 |
| 6.964 | 6.965 | 6.362 | 6.363 | 6.359 | 6.359 | 6.359 | 6.364 | 6.359 | 6.356 |
| 6.033 | 6.031 | 6.034 | 6.031 | 6.035 | 6.033 | 6.031 | 6.03 | 5.881 | 5.882 |
| 5.882 | 5.881 | 5.887 | 5.885 | 5.884 | 5.887 | 6.615 | 6.614 | 6.616 | 6.621 |
| 6.619 | 6.62 | 6.617 | 6.622 | 7.757 | 7.755 | 7.758 | 7.759 | 7.758 | 7.76 |
| 7.756 | 7.753 | 8.882 | 8.882 | 8.886 | 8.884 | 8.885 | 8.881 | 8.874 | 8.886 |
| 9.385 | 9.387 | 9.383 | 9.384 | 9.386 | 9.382 | 9.381 | 9.38 | 9.774 | 9.778 |
| 9.777 | 9.781 | 9.779 | 9.779 | 9.782 | 9.773 | 10.151 | 10.152 | 10.154 | 10.151 |
| 10.15 | 10.151 | 10.148 | 10.147 | 10.262 | 10.261 | 10.264 | 10.263 | 10.262 | 10.26 |
| 10.264 | 10.258 | 10.245 | 10.247 | 10.244 | 10.245 | 10.245 | 10.247 | 10.243 | 10.247 |
| 10.715 | 10.717 | 10.721 | 10.719 | 10.716 | 10.72 | 10.716 | 10.714 | 9.854 | 9.854 |
| 9.854 | 9.85 | 9.854 | 9.85 | 9.853 | 9.851 | 9.003 | 9.003 | 9.003 | 8.999 |
| 9.003 | 9.004 | 9.004 | 9.007 | 8.443 | 8.449 | 8.445 | 8.447 | 8.445 | 8.445 |
| 8.445 | 8.447 | 8.753 | 8.756 | 8.752 | 8.757 | 8.757 | 8.75 | 8.752 | 8.753 |
| 9.308 | 9.308 | 9.307 | 9.304 | 9.304 | 9.307 | 9.307 | 9.307 | 9.861 | 9.862 |
| 9.861 | 9.862 | 9.861 | 9.864 | 9.86 | 9.866 | 10.444 | 10.446 | 10.441 | 10.442 |
| 10.444 | 10.446 | 10.443 | 10.441 | 10.753 | 10.751 | 10.753 | 10.751 | 10.753 | 10.752 |
| 10.745 | 10.749 | 11.128 | 11.129 | 11.13 | 11.128 | 11.131 | 11.127 | 11.126 | 11.13 |
| 10.852 | 10.852 | 10.85 | 10.847 | 10.848 | 10.847 | 10.841 | 10.848 | 10.82 | 10.821 |
| 10.821 | 10.821 | 10.82 | 10.822 | 10.825 | 10.82 | 10.711 | 10.711 | 10.71 | 10.709 |

TABLE 9 the testing samples of the dosage.

| | | | | | | | | | |
|---|---|---|---|---|---|---|---|---|---|
| 3.06 | 3.06 | 3.06 | 3.06 | 3.06 | 3.06 | 3.06 | 3.06 | 3.06 | 3.06 |
| 3.06 | 3.06 | 3.06 | 3.06 | 3.06 | 3.06 | 3.06 | 3.06 | 3.06 | 3.06 |
| 3.06 | 3.06 | 3.06 | 3.06 | 3.06 | 3.06 | 3.06 | 3.06 | 3.06 | 3.06 |
| 3.06 | 3.06 | 3.06 | 3.06 | 3.06 | 3.06 | 3.06 | 3.06 | 3.06 | 3.06 |
| 3.06 | 3.06 | 3.06 | 3.06 | 3.06 | 3.06 | 3.06 | 3.06 | 3.06 | 3.06 |
| 3.06 | 3.06 | 3.06 | 3.06 | 3.06 | 3.06 | 3.06 | 3.06 | 3.06 | 3.06 |
| 3.06 | 3.06 | 2.85 | 2.85 | 2.85 | 2.85 | 2.85 | 2.85 | 2.85 | 2.85 |
| 2.85 | 2.85 | 2.85 | 2.85 | 2.85 | 2.85 | 2.85 | 2.85 | 2.85 | 2.85 |
| 2.85 | 2.85 | 2.85 | 2.85 | 2.85 | 2.85 | 2.85 | 2.85 | 2.85 | 2.85 |

TABLE 9-continued the testing samples of the dosage.

| | | | | | | | | | |
|---|---|---|---|---|---|---|---|---|---|
| 2.85 | 2.85 | 2.85 | 2.85 | 2.85 | 2.85 | 2.85 | 2.85 | 2.85 | 2.85 |
| 2.85 | 2.85 | 2.85 | 2.85 | 2.85 | 2.85 | 2.85 | 2.85 | 2.85 | 2.85 |
| 2.85 | 2.85 | 2.85 | 2.85 | 2.85 | 2.85 | 2.85 | 2.85 | 2.85 | 2.85 |
| 2.85 | 2.85 | 2.85 | 2.85 | 2.85 | 2.85 | 2.85 | 2.85 | 2.85 | 2.85 |
| 2.85 | 2.85 | 2.85 | 2.85 | 2.85 | 2.85 | 2.85 | 2.85 | 2.85 | 2.85 |
| 2.85 | 2.85 | 2.85 | 2.85 | 2.85 | 2.85 | 2.85 | 2.85 | 2.85 | 2.85 |

TABLE 10 the testing samples of the oxidation-reduction potential.

| | | | | | | | | | |
|---|---|---|---|---|---|---|---|---|---|
| −290.51 | −279.75 | −261.8 | −245.97 | −236.03 | −226.23 | −219.8 | −215.44 | −211.2 | −209.01 |
| −203.83 | −199.64 | −248.11 | −247.15 | −245.92 | −229.97 | −213.18 | −203.45 | −197.8 | −193.7 |
| −191.37 | −195.28 | −200.81 | −207.67 | −215.68 | −226.18 | −241.7 | −256.14 | −270.16 | −283.04 |
| −296.56 | −307.68 | −321.6 | −330.84 | −354.98 | −363.44 | −369.96 | −376.27 | −385.81 | −400.21 |
| −409.35 | −409.56 | −413.54 | −416.41 | −417.14 | −416.34 | −414.43 | −415.94 | −417.05 | −418.72 |
| −415.12 | −418.88 | −415.63 | −415.63 | −422.72 | −418.06 | −421.36 | −424.44 | −422.91 | −426.33 |
| −425.24 | −419.54 | −425.15 | −421.38 | −423.45 | −425.27 | −425.08 | −427.67 | −427.88 | −429.48 |
| −427.91 | −429.6 | −430.4 | −430.38 | −431.79 | −432.36 | −429.46 | −430.19 | −426.61 | −426.82 |
| −427.77 | −425.48 | −429.13 | −430.99 | −427.74 | −430.12 | −429.37 | −415.8 | −392.69 | −374.34 |
| −341.81 | −318.94 | −312.23 | −319.69 | −311 | −304.03 | −287.52 | −271.6 | −258.31 | −244.15 |
| −233.48 | −223 | −215.32 | −209.41 | −203.1 | −196.01 | −189.27 | −184.63 | −181.03 | −177.71 |
| −175.84 | −174.03 | −176.17 | −182.09 | −197.94 | −213.49 | −228 | −247.36 | −270.09 | −288.56 |
| −302.52 | −313.12 | −310.91 | −307.33 | −302.99 | −298.85 | −304.24 | −312.35 | −307.33 | −329.96 |
| −343.16 | −361.53 | −368.92 | −380.28 | −400.58 | −418.3 | −416.48 | −418.06 | −424.87 | −418.25 |
| −408.59 | −398.3 | −413.63 | −421.78 | −426.12 | −413.4 | −418.08 | −418.74 | −419.1 | −421.41 |

TABLE 11 the testing samples of the orthophosphate.

| | | | | | | | | | |
|---|---|---|---|---|---|---|---|---|---|
| 0.2587 | 0.2587 | 0.2775 | 0.2775 | 0.2841 | 0.2841 | 0.2999 | 0.3 | 0.3077 | 0.3077 |
| 0.2728 | 0.2728 | 0.1913 | 0.1912 | 0.1975 | 0.1975 | 0.1926 | 0.1926 | 0.1933 | 0.1933 |
| 0.1993 | 0.1993 | 0.2024 | 0.2024 | 0.1976 | 0.1975 | 0.2042 | 0.2042 | 0.2139 | 0.2139 |
| 0.2179 | 0.2178 | 0.2255 | 0.2255 | 0.2269 | 0.2269 | 0.2237 | 0.2238 | 0.2244 | 0.2245 |
| 0.2255 | 0.2255 | 0.2245 | 0.2245 | 0.2189 | 0.2189 | 0.2071 | 0.2071 | 0.205 | 0.205 |
| 0.2057 | 0.2056 | 0.2032 | 0.2032 | 0.2053 | 0.2053 | 0.1948 | 0.1948 | 0.1959 | 0.1958 |
| 0.2032 | 0.2032 | 0.2031 | 0.206 | 0.206 | 0.2015 | 0.2014 | 0.206 | 0.206 | 0.2025 |
| 0.2025 | 0.1917 | 0.1918 | 0.1956 | 0.1956 | 0.1858 | 0.1857 | 0.193 | 0.193 | 0.1773 |
| 0.1773 | 0.1895 | 0.1895 | 0.1913 | 0.1913 | 0.1934 | 0.1934 | 0.207 | 0.207 | 0.1962 |
| 0.1962 | 0.2175 | 0.2174 | 0.2132 | 0.2132 | 0.2146 | 0.2146 | 0.2163 | 0.2164 | 0.2118 |
| 0.2117 | 0.1915 | 0.1915 | 0.1768 | 0.1768 | 0.171 | 0.1709 | 0.1681 | 0.1682 | 0.1664 |
| 0.1664 | 0.1702 | 0.1702 | 0.1532 | 0.1531 | 0.181 | 0.1873 | 0.1872 | 0.1987 | 0.1988 |
| 0.2001 | 0.2001 | 0.2011 | 0.2011 | 0.2112 | 0.2112 | 0.2161 | 0.2161 | 0.2322 | 0.2321 |
| 0.2252 | 0.2251 | 0.2314 | 0.2314 | 0.2307 | 0.2307 | 0.2339 | 0.2338 | 0.2265 | 0.2265 |
| 0.2231 | 0.2231 | 0.2162 | 0.2162 | 0.212 | 0.212 | 0.203 | 0.203 | 0.2041 | 0.204 |

TABLE 12 the testing samples of the pH value.

| | | | | | | | | | |
|---|---|---|---|---|---|---|---|---|---|
| 7.3 | 7.26 | 7.22 | 7.2 | 7.21 | 7.26 | 7.28 | 7.29 | 7.3 | 7.29 |
| 7.3 | 7.31 | 7.23 | 7.41 | 7.5 | 7.46 | 7.39 | 7.34 | 7.29 | 7.26 |
| 7.24 | 7.44 | 7.45 | 7.4 | 7.35 | 7.28 | 7.21 | 7.17 | 7.15 | 7.55 |
| 7.57 | 7.53 | 7.49 | 7.46 | 7.43 | 7.39 | 7.36 | 7.62 | 7.53 | 7.42 |
| 7.34 | 7.26 | 7.18 | 7.13 | 7.1 | 7.48 | 7.51 | 7.48 | 7.45 | 7.41 |
| 7.39 | 7.37 | 7.35 | 7.53 | 7.53 | 7.48 | 7.44 | 7.41 | 7.38 | 7.36 |
| 7.35 | 7.53 | 7.49 | 7.43 | 7.37 | 7.3 | 7.25 | 7.2 | 7.17 | 7.36 |
| 7.36 | 7.33 | 7.28 | 7.21 | 7.16 | 7.14 | 7.14 | 7.29 | 7.32 | 7.32 |
| 7.32 | 7.3 | 7.28 | 7.27 | 7.27 | 7.35 | 7.35 | 7.33 | 7.31 | 7.3 |
| 7.28 | 7.27 | 7.28 | 7.32 | 7.3 | 7.28 | 7.26 | 7.22 | 7.21 | 7.23 |
| 7.25 | 7.49 | 7.49 | 7.41 | 7.32 | 7.26 | 7.23 | 7.21 | 7.21 | 7.51 |
| 7.51 | 7.44 | 7.35 | 7.3 | 7.34 | 7.59 | 7.64 | 7.7 | 7.62 | 7.54 |
| 7.46 | 7.44 | 7.39 | 7.35 | 7.3 | 7.57 | 7.53 | 7.49 | 7.46 | 7.44 |
| 7.43 | 7.42 | 7.41 | 7.71 | 7.79 | 7.77 | 7.75 | 7.73 | 7.71 | 7.71 |
| 7.73 | 7.82 | 7.73 | 7.63 | 7.54 | 7.46 | 7.41 | 7.36 | 7.33 | 7.59 |

TABLE 13 the testing samples of the ammonia nitrogen.

| | | | | | | | | | |
|---|---|---|---|---|---|---|---|---|---|
| 50.03 | 50.05 | 50.05 | 50.03 | 50.16 | 50.01 | 45.05 | 45.19 | 45.09 | 45.1 |
| 45.14 | 45.1 | 49.03 | 49.13 | 43.27 | 43.28 | 43.27 | 43.31 | 43.27 | 43.28 |
| 43.27 | 43.28 | 37.35 | 37.35 | 37.35 | 37.35 | 37.35 | 37.34 | 37.35 | 37.35 |
| 30.73 | 30.72 | 30.72 | 30.72 | 30.72 | 30.76 | 30.75 | 30.73 | 38.14 | 38.14 |
| 38.16 | 38.18 | 38.14 | 38.14 | 38.14 | 38.14 | 46.08 | 46.09 | 46.09 | 46.1 |
| 46.08 | 46.08 | 46.08 | 46.12 | 54.53 | 54.41 | 54.39 | 54.39 | 54.39 | 54.39 |
| 54.39 | 54.39 | 50.03 | 50.03 | 50.03 | 50.03 | 50.03 | 50.03 | 50.03 | 50.03 |
| 51.08 | 51.08 | 51.08 | 51.08 | 51.08 | 51.08 | 51.08 | 51.08 | 52.22 | 52.22 |
| 52.23 | 52.12 | 52.1 | 52.22 | 52.1 | 52.26 | 55.65 | 55.58 | 55.59 | 55.53 |
| 55.64 | 55.53 | 55.56 | 55.58 | 57.93 | 57.95 | 57.95 | 57.95 | 57.95 | 57.93 |
| 57.95 | 57.93 | 61.73 | 61.73 | 61.73 | 61.73 | 61.73 | 61.73 | 61.74 | 61.75 |
| 55.6 | 55.59 | 55.58 | 55.58 | 55.59 | 55.59 | 55.6 | 55.6 | 63.05 | 63.1 |
| 63.06 | 63 | 63.04 | 63.04 | 63.04 | 63.02 | 67.16 | 67.16 | 67.16 | 67.16 |
| 67.16 | 67.17 | 67.17 | 67.17 | 67.17 | 67.19 | 67.17 | 67.17 | 67.17 | 67.17 |
| 67.17 | 67.17 | 71.56 | 71.54 | 71.57 | 71.59 | 71.59 | 71.59 | 71.58 | 71.58 |

TABLE 14 the testing samples of the nitrate nitrogen.

| | | | | | | | | | |
|---|---|---|---|---|---|---|---|---|---|
| 7.99 | 7.65 | 7.11 | 6.78 | 5.99 | 5.5 | 5.38 | 4.91 | 4.73 | 3.25 |
| 3.94 | 3.43 | 4.38 | 5.72 | 5.74 | 5.1 | 4.36 | 4.09 | 3.67 | 4.22 |
| 4.27 | 5.12 | 4.89 | 4.58 | 4.87 | 4.93 | 4.65 | 4.88 | 5.06 | 4.93 |
| 5.25 | 5 | 5.09 | 5.39 | 5.37 | 5.89 | 6.01 | 5.97 | 5.9 | 6.28 |
| 6.59 | 6.17 | 6.34 | 6.61 | 6.35 | 5.92 | 7.13 | 6.6 | 6.81 | 6.56 |
| 6.89 | 6.57 | 6.85 | 6.68 | 6.76 | 6.81 | 6.89 | 6.33 | 6.55 | 6.87 |
| 6.64 | 6.97 | 7.06 | 6.62 | 6.62 | 6.42 | 6.79 | 6.62 | 6.57 | 6.4 |
| 6.48 | 6.75 | 6.61 | 6.35 | 7.02 | 6.19 | 6.43 | 6.39 | 6.66 | 6.55 |
| 6.48 | 6.41 | 6.07 | 6.21 | 7.02 | 6.35 | 6.95 | 6.13 | 5.23 | 4.9 |
| 4.1 | 3.72 | 3.18 | 3.43 | 3.5 | 2.94 | 2.84 | 2.9 | 2.57 | 3.67 |
| 3.29 | 3.18 | 3.65 | 3.69 | 4.13 | 4.24 | 3.52 | 3.52 | 4.3 | 5.31 |
| 5.21 | 4.46 | 4.47 | 4.66 | 4.34 | 4.41 | 4.88 | 4.7 | 4.68 | 4.79 |
| 4.92 | 4.99 | 5.12 | 4.71 | 3.88 | 3.42 | 3.05 | 2.48 | 2.87 | 1.89 |
| 1.76 | 1.74 | 1.92 | 1.78 | 1.39 | 1.21 | 1.27 | 0.85 | 1.6 | 1.31 |
| 1.45 | 1.39 | 1.14 | 1.15 | 1.12 | 0.99 | 1 | 1.31 | 0.95 | 1.76 |

TABLE 15 the testing samples of the chemical oxygen demand.

| | | | | | | | | | |
|---|---|---|---|---|---|---|---|---|---|
| 217.15 | 215.08 | 214.11 | 214.55 | 212.71 | 212.16 | 212.93 | 154 | 154.1 | 214 |
| 212.71 | 212.71 | 201.22 | 201.86 | 202.41 | 202.52 | 152.04 | 222.88 | 240.44 | 251.27 |
| 246.72 | 238.59 | 169.71 | 169.81 | 228.61 | 228.63 | 230.89 | 232.2 | 235.56 | 237.5 |
| 241.51 | 248.01 | 250.83 | 249.43 | 250.51 | 250.08 | 252.9 | 260.36 | 269.25 | 270.11 |
| 261.67 | 254.42 | 249.98 | 249.75 | 252.68 | 252.79 | 253.65 | 252.47 | 250.3 | 251.49 |
| 249.21 | 249.21 | 249.86 | 253.33 | 255.17 | 259.61 | 260.27 | 262 | 262.21 | 259.72 |
| 257.77 | 253.76 | 251.92 | 252.67 | 256.46 | 256.57 | 255.59 | 256.36 | 257.77 | 260.58 |
| 261.33 | 261.56 | 259.81 | 259.71 | 260.9 | 257.86 | 251.59 | 243.25 | 241.08 | 241.39 |
| 246.38 | 245.95 | 246.92 | 246.92 | 247.03 | 244.64 | 242.6 | 241.06 | 238.91 | 236.96 |
| 171.86 | 41.22 | 39.26 | 41.77 | 40.79 | 41.11 | 44.04 | 44.36 | 44.48 | 41.98 |
| 43.71 | 44.7 | 46.31 | 45.02 | 167.52 | 223.1 | 222.99 | 221.37 | 219.62 | 219.41 |
| 219.29 | 231.01 | 249.96 | 260.03 | 255.49 | 185.19 | 37.65 | 41.22 | 263.4 | 250.82 |
| 243.79 | 239.67 | 239.03 | 243.03 | 246.72 | 249.32 | 249.85 | 251.71 | 252.34 | 254.74 |
| 254.94 | 253.11 | 251.47 | 251.92 | 252.57 | 251.27 | 250.4 | 247.7 | 247.26 | 245.63 |
| 107.96 | 40.79 | 180.32 | 248.46 | 249.43 | 250.18 | 247.9 | 245.31 | 244.12 | 245.63 |

TABLE 16 the testing samples of the total nitrogen.

| | | | | | | | | | |
|---|---|---|---|---|---|---|---|---|---|
| 10.707 | 10.711 | 10.707 | 8.86 | 8.858 | 7.858 | 7.862 | 7.859 | 6.39 | 6.384 |
| 6.385 | 6.384 | 6.584 | 7.589 | 7.586 | 7.584 | 6.586 | 6.589 | 6.59 | 6.585 |
| 6.48 | 6.48 | 6.478 | 6.479 | 6.482 | 6.476 | 6.473 | 6.478 | 7.381 | 7.384 |
| 7.381 | 7.384 | 7.383 | 7.381 | 7.38 | 8.381 | 8.871 | 8.868 | 8.871 | 8.869 |
| 8.871 | 8.866 | 8.871 | 8.871 | 9.268 | 9.269 | 9.27 | 9.271 | 9.269 | 10.271 |
| 10.271 | 10.27 | 10.489 | 10.492 | 10.492 | 10.488 | 9.99 | 9.99 | 9.99 | 9.992 |
| 10.139 | 10.142 | 10.14 | 10.141 | 10.138 | 10.136 | 10.136 | 10.138 | 10.144 | 10.145 |
| 10.147 | 10.144 | 10.144 | 10.141 | 10.143 | 10.142 | 9.877 | 9.876 | 9.876 | 9.877 |
| 9.879 | 9.879 | 9.88 | 9.873 | 9.658 | 10.161 | 10.156 | 9.158 | 9.155 | 9.156 |
| 7.157 | 7.154 | 6.773 | 6.768 | 6.77 | 6.77 | 6.768 | 6.771 | 6.767 | 6.768 |
| 5.875 | 5.873 | 5.875 | 5.871 | 5.873 | 5.872 | 5.871 | 5.871 | 6.422 | 6.423 |
| 6.424 | 6.423 | 6.425 | 6.424 | 6.422 | 6.425 | 6.195 | 6.194 | 6.195 | 6.497 |
| 6.494 | 7.196 | 7.199 | 7.195 | 6.125 | 6.124 | 6.128 | 6.128 | 6.126 | 6.123 |
| 6.124 | 6.126 | 6.316 | 6.319 | 6.314 | 6.32 | 6.319 | 6.319 | 6.315 | 6.319 |
| 6.522 | 6.524 | 6.524 | 6.52 | 6.52 | 6.523 | 6.519 | 6.523 | 6.536 | 6.534 |

What is claimed is:

1. A total nitrogen intelligent detection method based on multi-objective optimized fuzzy neural network, the method comprising following steps:

(1) selecting input variables and collecting data by transmission devices; first, using a least square method to extract feature variables, wherein dosage, oxidation-reduction potential, orthophosphate, pH, ammonia nitrogen, nitrate-nitrogen and chemical oxygen demand are the feature variables that affect total nitrogen concentration; measuring each of the feature variables by a dosage device, an oxidation-reduction potential sensor, an orthophosphate sensor, a pH detector, an ammonia nitrogen sensor, a nitrate-nitrogen sensor and a chemical oxygen demand sensor, respectively, and then transmitting the measured feature variables to a computer via an optical fiber communication network, wherein the transmitted feature variables will be applied to the multi-objective optimized fuzzy neural network; wherein the dosage device is located at an end of an aerobic tank, the oxidation-reduction potential sensor is located in a middle of an anaerobic tank, the orthophosphate sensor is located at the end of the aerobic tank, the pH detector is located in an inlet cell, the ammonia nitrogen sensor is located in the inlet cell, the nitrate-nitrogen sensor is located at an end of an anoxic tank and the chemical oxygen demand sensor is located at an end of a primary sedimentation tank, the sensors use probes to detect concentration amounts for the respective feature variables, and the dosage device uses a flow meter to detect a concentration amount for the dosage feature variable; and obtaining the feature variables by using devices, wherein the feature variables are normalized to [0, 1];

(2) building a total nitrogen intelligent detection model based on a fuzzy neural network, the fuzzy neural network contains four layers: an input layer, a membership function layer, a rule layer and an output layer; the fuzzy neural network is 7-P-Q-1, including 7 neurons in the input layer, P neurons in the membership function layer, Q neurons in the rule layer and 1 neuron in the output layer, P and Q are positive integers between [2, 15], and P=Q; the number of training samples is N, an input of the fuzzy neural network is $x(n)=[x_1(n), x_2(n), \ldots, x_7(n)]$, $x_1(n)$ represents the dosage in nth training sample; $x_2(n)$ represents the oxidation-reduction potential in the middle of the anaerobic tank in nth training sample, $x_3(n)$ represents the orthophosphate at the end of the aerobic tank in nth training sample, $x_4(n)$ represents pH in the inlet cell in nth training sample, $x_5(n)$ represents the ammonia nitrogen in the inlet cell in nth training sample, $x_6(n)$ represents the nitrate nitrogen at the end of the anoxic tank in nth training sample, and $x_7(n)$ represents the chemical oxygen demand of a primary sedimentation tank in nth training sample, an output of the fuzzy neural network is y(n) which represents predicted total nitrogen concentration in nth training sample and an actual output is $\hat{y}(n)$ which represents an actual total nitrogen concentration in nth training sample measured by a total nitrogen sensor, $n=1, 2, \ldots, N$; the fuzzy neural network includes:

① input layer: there are 7 neurons in the input layer, an output of the input layer is:

$$u_m(n)=x_m(n), m=1,2,\ldots,7 \qquad (1)$$

where $u_m(n)$ is mth output value, $m=1, 2, \ldots, 7$;

② Membership function layer: there are P neurons in the membership function layer, an output of the membership function layer is:

$$\varphi_p(n) = \prod_{i=1}^{7} e^{-\frac{(u_m(n)-\mu_{mp}(n))^2}{2\sigma_p^2(n)}} = e^{-\sum_{m=1}^{7}\frac{(u_m(n)-\mu_{mp}(n))^2}{2\sigma_p^2(n)}}, \qquad (2)$$

$$p = 1, 2, \ldots, P$$

where $\mu_{mp}(n)$ is a center of pth membership function neuron with mth input, $\sigma_p(n)$ is a standard deviation of pth membership function neuron, $\varphi_p(n)$ is an output value of pth membership function;

③ rule layer: there are Q neurons in the rule layer, and an output value of the rule layer is:

$$\eta_q(n) = \varphi_q(n) / \sum_{p=1}^{P} \varphi_p(n), q = 1, 2, \ldots, Q \qquad (3)$$

where $\eta_q(n)$ is an output of qth neuron;

④ output layer: there is 1 neuron in the output layer, and an output value of the output layer is y(n):

$$y(n) = \sum_{q=1}^{Q} w_q(n)\eta_q(n), q = 1, 2, \ldots, Q \qquad (4)$$

where $w_q(n)$ is connection weight between qth neuron in the rule layer and the neuron in the output layer;

(3) training the total nitrogen intelligent detection model based on a multi-objective particle swarm optimization algorithm by:

① in the fuzzy neural network, each variable in an initial center vector $\mu_q(1)$ is randomly selected in an interval $[-1, 1]$, an initial width $\sigma_q(1)$ is assigned to 1, $q=1, 2, \ldots, Q$; each variable in an initial connection weight vector w(1) is randomly selected in an interval $[-1, 1]$; and set a current iteration number $t=1$;

② Set maximum number of iterations is $T_{max}$, $T_{max} \in [200, 500]$; the number of particles in a population of the multi-objective particle swarm optimization algorithm is L, $L \in [50, 150]$, and each particle represents a fuzzy neural network; maximum number of neurons in the rule layer is 15, and fixed maximum dimension of the particles is set to 135, so that each particle is represented by a 135-dimensional row vector; position and velocity of lth particle can be expressed as:

$$a_l(1)=[\mu_{l,1}(1),\sigma_{l,1}(1),w_{l,1}(1),\mu_{l,2}(1),\sigma_{l,2}(1),$$
$$w_{l,2}(1), \ldots, \mu_{l,Q_l(1)}(1),\sigma_{l,Q_l(1)}(1),w_{l,Q_l(1)}(1)] \qquad (5)$$

$$v_l(1)=[v_{l,1}(1),v_{l,2}(1),\ldots,v_{l,9Q_l(1)}(1)] \qquad (6)$$

where $l=1, 2, \ldots, L$, $a_l(1)$ represents a position vector of initial lth particle, $\mu_{l,k}(1)$, $\sigma_{l,k}(1)$, $w_{l,k}(1)$ represent a center vector, width and connection weight of kth neuron in the rule layer corresponding to the initial lth particle, respectively, $k=1, 2, \ldots, Q_l(1)$, $Q_l(1)$ is the number of neurons in the rule layer corresponding to the initial lth particle, $v_l(1)$ represents an initial velocity vector of lth particle; an initial position vector $a_l(1)$ is determined by parameters and structure of initial fuzzy neural network; each variable of the initial velocity vector $v_l(1)$ can take any value in $[-0.5, 0.5]$; initial effective dimension of the lth particle is $9Q_l(1)$; when an effective particle dimension is less than 135, values of remaining dimensions are filled with 0 to ensure consistency of particle dimensions in the population;

③ objective functions of the multi-objective particle swarm optimization algorithm include accuracy and complexity of the fuzzy neural network; the accuracy of the fuzzy neural network is represented by a root mean square error, so a first objective function is:

$$f_1(a_l(t)) = \sqrt{\sum_{n=1}^{N}(y_l(n) - \hat{y}(n))^2 / N} \qquad (7)$$

where $y_l(n)$ is the output of the fuzzy neural network, representing the predicted total nitrogen concentration in nth training sample and corresponding to the lth particle $a_l(t)$, $\hat{y}(n)$ is the actual total nitrogen concentration in nth training sample, and $f_1(a_l(t))$ is a first objective function value corresponding to the particle $a_l(t)$ at lth iteration; in addition, a second objective function based on structure complexity is designed as:

$$f_2(a_l(t)) = (15Q_l(t)\log N + 2\log Q_l(t))\sum_{n=1}^{N}(y_l(n) - \hat{y}(n))^2 \Big/ N\sum_{n=1}^{N}(\hat{y}(n) - \bar{y})^2 \quad (8)$$

$$\bar{y} = \sum_{n=1}^{N}\hat{y}(n)/N \quad (9)$$

where $Q_l(t)$ is the number of neurons in a layer corresponding to the lth particle at th iteration, $\bar{y}$ is an average value of the actual total nitrogen concentration in the N training samples, $f_2(a_l(t))$ is a second objective function value corresponding to the particle $a_l(t)$ at tth iteration;

④ according to the first and second objective function values $f_1(a_l(t))$ and $f_2(a_l(t))$ of the multi-objective particle swarm optimization algorithm, crowded distances of particles in an objective space and a decision space are as follows:

$$S_O(a_l(t)) = \sqrt{\sum_{j=1}^{L}\left((f_1(a_l(t)) - f_1(a_j(t)))^2 + (f_2(a_l(t)) - f_2(a_j(t)))^2\right)} \quad (10)$$

$$S_D(a_l(t)) = \sqrt{\sum_{j=1}^{L}(a_l(t) - a_j(t))^2} \quad (11)$$

where $S_O(a_l(t))$ is a crowded distance of the particle $a_l(t)$ in the objective space at tth iteration, and $S_D(a_l(t))$ is a crowded distance of the particle $a_l(t)$ in the decision space at tth iteration; based on the diversity and convergence of particles, a global optimal particle is selected:

$$G_R(a_l(t)) = \frac{\sqrt{(f_1(a_l(t)))^2 + (f_2(a_l(t)))^2}}{S'_O(a_l(t)) + S'_D(a_l(t))} \quad (12)$$

where $G_R(a_l(t))$ is a comprehensive index value of particle $a_l(t)$ in the population at tth iteration, as well as $S'_O(a_l(t))$ and $S'D(a_l(t))$ are respectively $S_O(a_l(t))$ and $S_D(a_l(t))$ normalized crowding distance; the particle $a_l(t)$ with smallest $G_R(a_l(t))$ value in the population is the global optimal particle at tth iteration;

⑤ dth dimensional velocity and position of the particle is updated:

$$v_{l,d}(t+1) = \omega v_{l,d}(t) + c_1 r_1(p_{l,d}(t) - \alpha_{l,d}(t)) + c_2 r_2(g_d(t) - \alpha_{l,d}(t)) \quad (13)$$

$$\alpha_{l,d}(t+1) = \alpha_{l,d}(t) + v_{l,d}(t+1) \quad (14)$$

where $v_{l,d}(t)$ represents the dth dimensional velocity of the lth particle at tth iteration, $a_{l,d}(t)$ represents the dth dimensional position of the lth particle at tth iteration, $v_{l,d}(t+1)$ and $a_{l,d}(t+1)$ represent the dth dimensional velocity and position of the lth particle at the t+1 iteration, d=1, 2, ..., 135; an extra particle dimension is set to 0; $\omega$ is a weight of inertia, $\omega$ can be arbitrarily selected in [0, 1], $c_1$ is individual learning factors, and $c_1$ is arbitrarily selected in [1.5, 2]; $c_2$ is global learning factors, and $c_2$ is arbitrarily selected in [1.5, 2]; $r_1$ and $r_2$ represent random values uniformly distributed between [0, 1], $p_l(t) = [p_{l,1}(t), p_{l,2}(t), \ldots, p_{l,135}(t)]$, $p_l(t)$ is the lth individual optimal particle at tth iteration, $g(t) = [g_1(t), g_2(t), \ldots, g_{135}(t)]$, $g(t)$ is the global optimal particle at tth iteration;

⑥ if mod (t, 5)≠0 and t<$T_{max}$, the number of iterations t will increase by 1, and go to step ③; if mod (t, 5)=0 and t<$T_{max}$, go to step ⑦; if t=$T_{max}$, stop training process; mod ( ) is the remainder operation;

⑦ update rules of the fuzzy neural network structure are as follows:

$$Q_l(t+1) = Q_l(t) + h \quad (15)$$

$$Q_{ave}(t) = \sum_{i=0}^{4} Q_g(t-i)/5 \quad (16)$$

when $Q_{ave}(t) < Q_l(t)$, h=−1; when $Q_{ave}(t) = Q_l(t)$, h=0; when $Q_{ave}(t) > Q_l(t)$, h=1; $Q_g(t)$ is the number of neurons in the rule layer corresponding to the global optimal particle g(t) at tth iteration, i is the difference with the current iteration number, i=0, 1, ..., 4, $Q_l(t+1)$ represents the number of neurons in the rule layer corresponding to the t+1 iteration of the lth particle;

⑧ if t<$T_{max}$, the number of iterations t increase by 1, and go to step ③; if t=$T_{max}$, stop the training process;

(4) applying input to the trained intelligent detection model, wherein the input comprises the dosage, the oxidation-reduction potential in the middle of the anaerobic tank, the orthophosphate at the end of the aerobic tank, pH in the inlet cell, the ammonia nitrogen in the inlet cell, the nitrate-nitrogen at the end of the anoxic tank and the chemical oxygen demand of the primary sedimentation tank; obtaining an output value of the total nitrogen intelligent detection model which represents a predicted total nitrogen concentration that is normalized to [0, 1] and de-normalizing the output value of the total nitrogen intelligent detection model to obtain a predicted total nitrogen concentration.

2. The total nitrogen intelligent detection method based on multi-objective optimized fuzzy neural network of claim 1, wherein the transmission devices are used to transmit the received real-time data information to the fuzzy neural network as the input; data sets in the sensors are transmitted to the computer through the optical fiber communication network, and the computer is sent to the total nitrogen intelligent detection model by the Ethernet to obtain the predicted total nitrogen concentration.

\* \* \* \* \*